(12) United States Patent
Minteer et al.

(10) Patent No.: US 8,048,660 B2
(45) Date of Patent: Nov. 1, 2011

(54) IMMOBILIZED ENZYMES AND USES THEREOF

(75) Inventors: Shelley D. Minteer, Pacific, MO (US);
Niki L. Akers, St. Louis, MO (US);
Christine M. Moore, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 12/576,014

(22) Filed: Oct. 8, 2009

(65) Prior Publication Data

US 2010/0041123 A1 Feb. 18, 2010

Related U.S. Application Data

(62) Division of application No. 10/617,452, filed on Jul. 11, 2003, now Pat. No. 7,638,228.

(60) Provisional application No. 60/486,076, filed on Jul. 10, 2003, provisional application No. 60/429,829, filed on Nov. 27, 2002.

(51) Int. Cl.
*C12N 11/02* (2006.01)
*C12N 11/08* (2006.01)
(52) U.S. Cl. .................................. 435/177; 435/180
(58) Field of Classification Search .................. None
See application file for complete search history.

(56) References Cited

U.S. PATENT DOCUMENTS

| | | | |
|---|---|---|---|
| 4,117,202 A | 9/1978 | Beck | |
| 4,207,076 A | 6/1980 | Bove et al. | |
| 4,224,125 A | 9/1980 | Nakamura et al. | |
| 4,490,464 A | 12/1984 | Gorton et al. | |
| 4,705,503 A | 11/1987 | Dorman et al. | |
| 4,761,209 A | 8/1988 | Bonaventura et al. | |
| 5,211,984 A | 5/1993 | Wilson | |
| 5,262,035 A | 11/1993 | Gregg et al. | |
| 5,262,305 A | 11/1993 | Heller et al. | |
| 5,264,092 A | 11/1993 | Skotheim et al. | |
| 5,264,105 A | 11/1993 | Gregg et al. | |
| 5,320,725 A | 6/1994 | Gregg et al. | |
| 5,356,786 A | 10/1994 | Heller et al. | |
| 5,393,615 A | 2/1995 | Corey et al. | |
| 5,521,101 A | 5/1996 | Saini et al. | |
| 5,593,852 A | 1/1997 | Heller et al. | |
| 5,665,222 A | 9/1997 | Heller et al. | |
| 5,718,947 A | 2/1998 | Martin et al. | |
| 5,820,551 A | 10/1998 | Hill et al. | |
| 5,919,583 A | 7/1999 | Grot et al. | |
| 5,958,199 A | 9/1999 | Miyamoto et al. | |
| 6,294,281 B1 | 9/2001 | Heller | |
| 6,294,291 B1 | 9/2001 | Ozaki et al. | |
| 6,387,625 B1 | 5/2002 | Eckhardt et al. | |
| 6,460,733 B2 | 10/2002 | Acker et al. | |
| 6,500,571 B2 | 12/2002 | Liberatore et al. | |
| 6,531,239 B2 | 3/2003 | Heller | |
| 2002/0025456 A1 | 2/2002 | Gieshoff et al. | |
| 2002/0025469 A1 | 2/2002 | Heller | |
| 2002/0122972 A1 | 9/2002 | Klitsner et al. | |
| 2002/0127440 A1 | 9/2002 | Yamamoto et al. | |
| 2003/0027023 A1 | 2/2003 | Dutil et al. | |
| 2003/0039868 A1 | 2/2003 | Liberatore et al. | |
| 2003/0087144 A1 | 5/2003 | Sun et al. | |
| 2003/0148169 A1 | 8/2003 | Willner et al. | |
| 2003/0164335 A1 | 9/2003 | Grate et al. | |
| 2003/0198858 A1 | 10/2003 | Sun et al. | |
| 2004/0101741 A1 | 5/2004 | Minteer et al. | |
| 2004/0121018 A1 | 6/2004 | Grate et al. | |
| 2004/0214053 A1 | 10/2004 | Armstrong | |
| 2004/0217016 A1 | 11/2004 | Khan | |
| 2005/0095466 A1 | 5/2005 | Minteer et al. | |
| 2005/0101841 A9 | 5/2005 | Kaylor et al. | |

FOREIGN PATENT DOCUMENTS

| | | |
|---|---|---|
| EP | 0 300 802 A2 | 1/1989 |
| EP | 0 667 397 A1 | 8/1995 |
| EP | 0 747 984 A2 | 12/1996 |
| WO | 90/05910 A1 | 5/1990 |
| WO | 99/38002 A1 | 7/1999 |
| WO | 00/22688 A3 | 4/2000 |
| WO | 03/006713 A1 | 1/2003 |
| WO | 03/019170 A1 | 3/2003 |
| WO | 03/019705 A2 | 3/2003 |
| WO | 03/067697 A2 | 8/2003 |
| WO | 03/106966 A2 | 12/2003 |
| WO | 2004/079848 A2 | 9/2004 |
| WO | 2005/096430 A1 | 10/2005 |

OTHER PUBLICATIONS

Karyakin et al, Analytical Chemistry, 2002 (epub ahead of print: Mar. 5, 2002), vol. 74, pp. 1597-1603.*
Advanced Enzymes "Glucose Oxidase, Enzyme, Glucose Oxidase Test, Glucose Oxidase Reaction, Glucose Oxidase Method, Glucose Oxidase Assay" accessed Mar. 12, 2008 at http://www.enzymeindia.com/enzymes/glucose-oxidase.asp.
"Alcohol Dehydrogenase" Worthington Enzyme Manual, accessed Nov. 4, 2003 at http://www.worthington-biochem.com/ADH/default.html.
Bahar, T., et al., "Immobilization of Alpha-Chymotrypsin onto Newly Produced Poly(Hydroxypropyl Methacrylate-co-methacrylic Acid) Hydrogel Beads," Reactive & Functional Polymers, 2000, pp. 71-78, vol. 44.
Blaedel, W. J., et al., "Study of the Electrochemical Oxidation of Reduced Nicotinamide Adenine Dinucleotide," Analytical Chemistry, Jul. 1975, pp. 1337-1343, vol. 47, No. 8.
Bogdanovskaya, V. A., et al., "Electroreduction of Oxygen on Carbon Black with Absorbed Peroxidase or a Peroxidase-Nafion Composite," Russian Journal of Electrochemistry, 2000, pp. 874-878, vol. 36, No. 8.

(Continued)

*Primary Examiner* — Allison Ford
(74) *Attorney, Agent, or Firm* — Senniger Powers LLP

(57) ABSTRACT

Disclosed are bioanodes comprising a quaternary ammonium treated Nafion® polymer membrane and a dehydrogenase incorporated within the treated Nafion® polymer. The dehydrogenase catalyzes the oxidation of an organic fuel and reduces an adenine dinucleotide. The ion conducting polymer membrane lies juxtaposed to a polymethylene green redox polymer membrane, which serves to electro-oxidize the reduced adenine dinucleotide. The bioanode is used in a fuel cell to produce high power densities.

20 Claims, 11 Drawing Sheets

OTHER PUBLICATIONS

Buttry, D. A., et al., "Electrochemical Control of the Luminescent Lifetime of Ru(bpy)32+* Incorporated in Nafion Films on Graphite Electrodes," Journal of the American Chemical Society, 1982, pp. 4824-4829, vol. 104, No. 18.

Chen, T., et al., "A Miniature Biofuel Cell," Journal of the American Chemical Society, 2001, pp. 8630-8631, vol. 123, No. 35.

Crecchio, C., et al., "Polyphenoloxidases Immobilized in Organic Gels: Properties and Applications in the Detoxification of Aromatic Compounds," Biotechnology and Bioengineering, Dec. 20, 1995, pp. 585-591, vol. 48, No. 6.

Davis, G., et al., "Bioelectrochemical Fuel Cell and Sensor Based on a Quinoprotein, Alcohol Dehydrogenase," Enzyme Microbial Technology, Sep. 1983, pp. 383-388, vol. 5.

Demirel, G., et al., "Semi-interpenetrating Polymer Networks (IPNs) for Entrapment of Glucose Isomerase," Reactive & Functional Polymers, 2006, pp. 389-394, vol. 66.

Durán, N., et al., "Applications of Laccases and Tyrosinases (Phenoloxidases) Immobilized on Different Supports: a Review," Enzyme and Microbial Technology, 2002, pp. 907-931, vol. 31.

Fadnavis, N. W., et al., "Immobilized Enzymes in Reverse Micelles: Studies with Gel-entrapped Trypsin and Alpha-Chymotrypsin in AOT Reverse Micelles," Biotechnology and Bioengineering, 1989, pp. 1277-1282, vol. 33.

Fernández-Sanchez, C., et al., "Voltammetric Monitoring of Laccase-catalysed Mediated Reactions," Bioelectrochemistry, 2002, pp. 149-156, vol. 58.

Frébortova, J., et al., "Intramolecular Electron Transport in Quinoprotein Alcohol Dehydrogenase of Acetobacter Methanolicus: A Redox-Titration Study," Biochemica et Biophysica Acta, 1998, pp. 24-34, vol. 1363.

Glucose Oxidase Pathway accessed on Mar. 12, 2008 at http://www.biochemj.org/bj/347/0553/bj3470553f03.gif.

Gouda, M. D., et al., "Stability Studies on Immobilized Glucose Oxidase Using an Amperometric Biosensor—Effect of Protein Based Stabilizing Agents," Electroanalysis, 2001, pp. 849-855, vol. 13, No. 10.

Green, D. W., et al., "Inversion of the Substrate Specificity of Yeast Alcohol Dehydrogenase," The Journal of Biological Chemistry, 1993, pp. 7792-7798, vol. 268, No. 11.

Guillén, F., et al., "Oxygen Activation During Oxidation of Methoxyhydroquinones by Laccase from *Pleurotus eryngii*," Applied and Environmental Microbiology, Jan. 2000, pp. 170-175, vol. 66, No. 1.

Hsu, A.-F., et al., "Immobilization of Lipoxygenase in an Alginate-silicate Solgel Matrix: Formation of Fatty Acid Hydroperoxides," Biotechnology Letters, Jan. 1997, pp. 71-74, vol. 19, No. 1.

Huang, H., et al., "Electrochemistry and Electrocatalysis with Heme Proteins in Chitosan Biopolymer Films," Analytical Biochemistry, 2002, pp. 141-151, vol. 308.

Ivnitski, D., et al., "Glucose Oxidase Anode for Biofuel Cell Based on Direct Electron Transfer," Electrochemistry Communications, 2006, pp. 1204-1210, vol. 8.

Jin, L., et al., "A Study of Uricase Biosensor Based on a Glassy Carbon Electrode Modified with Nafion and Methyl Viologen," Mikrochimica Acta, 1993, pp. 71-75, vol. 112.

Karyakin, A. A., et al., "Improvement of Electrochemical Biosensors Using Enzyme Immobilization from Water-Organic Mixtures with a High Content of Organic Solvent," Analytical Chemistry, Dec. 15, 1996, pp. 4335-4341, vol. 68, No. 24.

Kim, H. H., et al., "A Miniature Membrane-less Biofuel Cell Operating Under Physiological Conditions at 0.5 V," Journal of the Electrochemical Society, 2003, pp. A209-A213, vol. 150, No. 2.

Klotzbach, T., et al., "Effects of Hydrophobic Modification of Chitosan and Nafion on Transport Properties, Ion-Exchange Capacities, and Enzyme Immobilization," Journal of Membrane Science, 2006, pp. 276-283, vol. 282.

Krajewska, B., "Application of Chitin- and Chitosan-Based Materials for Enzyme Immobilizations: A Review," Enzyme and Microbial Technology, 2004, pp. 126-139, vol. 35.

Leonida, M. D., et al., "Co-Electropolymerization of a Viologen Oligomer and Lipoamide Dehydrogenase on an Electrode Surface. Application to Cofactor Regeneration," Bioorganic & Medicinal Chemistry Letters, 1996, pp. 1663-1666, vol. 6, No. 14.

Liu, C.-G., et al., "Self-Assembled Nanoparticles Based on Linoleic-Acid Modified Chitosan: Stability and Absorption of Trypsin," Carbohydrate Polymers, 2005, pp. 293-298, vol. 62.

Maalouf, R., et al., "Amperometric and Impedimetric Characterization of a Glutamate Biosensor Based on Nafion(R) and a Methyl Viologen Modified Glassy Carbon Electrode," Biosensors and Bioelectronics, 2007, pp. 2682-2688, vol. 22.

Mano, N., et al., "An Oxygen Cathode Operating in a Physiological Solution," Journal of the American Chemical Society, 2002, pp. 6480-6486, vol. 124, No. 22.

Ohara, T. J., et al., "Wired Enzyme Electrodes for Amperometric Determination of Glucose or Lactate in the Presence of Interfering Substances," Analytical Chemistry, Aug. 1, 1994, pp. 2451-2457, vol. 66, No. 15.

Ortiz, G., et al., "Graphite-Poly(tetrafluoroethylene) Composite Enzyme Electrodes as Suitable Biosensors in Predominantly Nonaqueous Media," Analytical Chemistry, Sep. 1, 1997, pp. 3521-3526, vol. 69, No. 17.

Palmore, G. T. R., et al., "A Methanol/Dioxygen Biofuel Cell That Uses NAD+-Dependent Dehydrogenases as Catalysts: Application of an Electro-Enzymatic Method to Regenerate Nicotinamide Adenine Dinucleotide at Low Overpotentials," Journal of Electroanalytical Chemistry, 1998, pp. 155-161, vol. 443.

Plotkin, E. V., et al., "Methanol Dehydrogenase Bioelectrochemical Cell and Alcohol Detector," Biotechnology Letters, 1981, pp. 187-192, vol. 3, No. 4.

Ryabova, E. S., et al., "Coordinative Approach to Mediated Electron Transfer: Ruthenium Complexed to Native Glucose Oxidase," Angew. Chem. Int. Ed., 1999, pp. 804-807, vol. 38, No. 6.

Schindler, J. G., et al., "Long-Functioning Beta-D-Glucose and L-Lactate Biosensors for Continuous Flow-Through Measurements for "Fouling"-Resistant and Selectivity-Optimized Serum- and Hemoanalysis," European Journal of Clinical Chemistry and Clinical Biochemistry, Aug. 1994, pp. 599-608, vol. 32, No. 8 (25 page translation is attached).

Schrenk, M. J., et al., "Effect of Mixture Casting Nafion® with Quaternary Ammonium Bromide Salts on the Ion-Exchange Capacity and Mass Transport in the Membranes," Journal of Membrane Science, 2002, pp. 3-10, vol. 205.

Suekane, M., "Immobilization of Glucose Isomerase," Zeitschrift for Allgemeine Mikrobiologie, 1982, pp. 565-576, vol. 22, No. 8.

Tayhas, G., et al., "Microbial and Enzymatic Biofuel Cells," in ACS Symposium Series 566, 1994, pp. 271-290.

Thomas, T. J., et al., "Effects of Annealing on Mixture-Cast Membranes of Nafion® and Quaternary Ammonium Bromide Salts," Journal of Membrane Science, 2003, pp. 55-66, vol. 213.

Trudeau, F., et al., "Reagentless Mediated Laccase Electrode for the Detection of Enzyme Modulators," Analytical Chemistry, Mar. 1, 1997, pp. 882-886, vol. 69, No. 5.

Tümtürk, H., et al., "The Effect of External Stimuli on the Invertase Adsorption Capacity of Poly(N-vinyl-2-pyrrolidone-co-itaconic Acid) Hydrogels," Die Angewandte Makromolekulare Chemie, 1999, pp. 1-5, vol. 273.

Vakurov, A. V., et al., "Dry Enzyme-Polymer Complexes: Stable Organosoluble Biocatalysts for Nonaqueous Enzymology," Biotechnology Letters, Feb. 1994, pp. 175-178, vol. 16, No. 2.

Yamada, Y., et al., "Effective Bioconversion with Continuous Product Recovery Using AOT/Lecithin Mixed Reverse Micellar Systems and Centrifugal Partition Chromatography as a Novel Bioreactor," Biotechnol. Prog., 1995, pp. 682-688, vol. 11, No. 6.

Yoshioka, H., et al., "Chitosan-Derived Polymer-Surfactants and Their Micellar Properties," Abstract, Biosci. Biotechnol. Biochem., Oct. 1995, pp. 1901-1904, vol. 59, No. 10.

Yue, P. L., et al., "Enzymatic Oxidation of C1 Compounds in a Biochemical Fuel Cell," Chemical Engineering Journal, 1986, pp. B69-B77, vol. 33.

Zawodzinski, T. A., et al., "Thin-Layer Composite Enzyme Electrodes for Glucose Determinations," Electroanalysis, 1995, pp. 1035-1040, vol. 7, No. 11.

Zhang, C., et al., "Evaluation of Substituted-1,10-phenanthroline Complexes of Osmium as Mediator for Glucose Oxidase of *Aspergillus niger*," Analytica Chimica Acta, 2000, pp. 225-232, vol. 408.

Zhou, D., et al., "The Electrochemical Polymerization of Methylene Green and its Electrocatalysis for the Oxidation of NADH," Analytica Chimica Acta, 1996, pp. 41-48, vol. 329.

\* cited by examiner

United States Patent US 8,048,660 B2

IMMOBILIZED ENZYMES AND USES THEREOF

CROSS-REFERENCE TO RELATED APPLICATIONS

This application is a Divisional Patent Application of U.S. patent application Ser. No. 10/617,452, filed Jul. 11, 2003, which is a non-provisional of U.S. Provisional Patent Application No. 60/486,076, filed Jul. 10, 2003, and U.S. Provisional Patent Application No. 60/429,829, filed Nov. 27, 2002.

BACKGROUND

Field of the Invention

The invention relates generally to fuel cells and methods of generating electricity. The invention relates specifically to anodes that contain biological enzymes incorporated within an immobilization material, such as an ion-conducting polymer and methods of generating electricity using same.

A biofuel cell is similar to a traditional polymer electrolyte membrane ("PEM") fuel cell in that it consists of a cathode and anode separated by a polymer electrolyte membrane. Biofuel cells differ from the traditional fuel cell by the material used to catalyze the electrochemical reaction. Rather than using precious metals as catalysts, biofuel cells rely on biological molecules such as enzymes to carry out the reaction. Although early biofuel cell technology employed metabolic pathways of whole microorganisms, the problems associated with this approach include low volumetric catalytic activity of the whole organism and impractical power density outputs [1]. Enzyme isolation techniques spurred advancement in biofuel cell applications by increasing volumetric activity and catalytic capacity [1]. Isolated enzyme biofuel cells yield increased power density output by overcoming interferences associated with cellular membrane impedance with electron transfer and lack of fuel consuming microbial growth.

Although enzymes are highly efficient catalysts, there have been problems incorporating them into fuel cells. Early enzyme-based fuel cells contained enzymes in solution rather than immobilized on the electrode surface [1 and references within, which are incorporated herein by reference]. Enzymes in solutions are only stable for days, whereas immobilized enzymes can be stable for months. One of the main obstacles of enzyme-based biofuel cells has been to immobilize the enzyme in a membrane at the electrode surface that will extend the lifetime of the enzyme and form a mechanically and chemically stable layer, while not forming a capacitive region at the electrode surface. In most $H_2/O_2$ fuel cells, the binder that holds the catalyst at the electrode surface is Nafion®. Nafion® is a perfluorinated ion exchange polymer that has excellent properties as an ion conductor. However, Nafion® has not been successful at immobilizing enzymes at the surface of biofuel cell electrodes because Nafion® forms an acidic membrane that decreases the lifetime and activity of the enzyme.

SUMMARY OF THE INVENTION

One of the various aspects of the present invention is a biofuel cell for generating electricity comprising: a fuel fluid, an electron mediator, a cathode capable of reducing an oxidant in the presence of electrons to form water, and a bioanode which comprises (a) an electron conductor, (b) at least one enzyme capable of reacting with an oxidized form of the electron mediator and the fuel fluid to produce an oxidized form of the fuel fluid and a reduced form of the electron mediator, (c) an enzyme immobilization material capable of immobilizing and stabilizing the enzyme, the material being permeable to the fuel fluid and the electron mediator, and (d) an electrocatalyst adjacent the electron conductor, an oxidized form of the electrocatalyst being capable of reacting with the reduced form of the electron mediator to produce an oxidized form of the electron mediator and a reduced form of the electrocatalyst, the reduced form of the electrocatalyst being capable of releasing electrons to the electron conductor.

Another aspect of the present invention is a biofuel cell for generating electricity comprising: a fuel fluid, a cathode capable of reducing an oxidant in the presence of electrons to form water, and a bioanode which comprises (a) an electron conductor, (b) at least one enzyme capable of reacting with an oxidized form of an electron mediator and the fuel fluid to produce an oxidized form of the fuel fluid and a reduced form of the electron mediator, (c) an enzyme immobilization material comprising the electron mediator, the enzyme immobilization material being capable of immobilizing and stabilizing the enzyme, the material being permeable to the fuel fluid, and (d) an electrocatalyst adjacent the electron conductor, an oxidized form of the electrocatalyst being capable of reacting with the reduced form of the electron mediator to produce an oxidized form of the electron mediator and a reduced form of the electrocatalyst, the reduced form of the electrocatalyst being capable of releasing electrons to the electron conductor.

A further aspect is a biofuel cell for generating electricity comprising: a fuel fluid, an electron mediator, a cathode capable of reducing an oxidant in the presence of electrons to form water, and a bioanode for oxidizing the fuel fluid to generate electricity, the bioanode comprising (a) an electron conductor, (b) at least one enzyme capable of reacting with an oxidized form of the electron mediator and the fuel fluid to produce an oxidized form of the fuel fluid and a reduced form of the electron mediator, the reduced form of the electron mediator being capable of releasing electrons to the electron conductor, and (c) an enzyme immobilization material capable of immobilizing and stabilizing the enzyme, the material being permeable to the fuel fluid and the electron mediator.

Yet another aspect is a biofuel cell for generating electricity comprising: a fuel fluid, a cathode capable of reducing an oxidant in the presence of electrons to form water, and a bioanode for oxidizing the fuel fluid to generate electricity, the bioanode comprising (a) an electron conductor, (b) at least one enzyme capable of reacting with an oxidized form of an electron mediator and the fuel fluid to produce an oxidized form of the fuel fluid and a reduced form of the electron mediator, the reduced form of the electron mediator being capable of releasing electrons to the electron conductor, and (c) an enzyme immobilization material comprising the electron mediator, the enzyme immobilization material being capable of immobilizing and stabilizing the enzyme, the material being permeable to the fuel fluid.

A further aspect is a method of generating electricity using the biofuel cell of any one of the above aspects of the invention.

Another aspect of the invention is an enzyme immobilized in a non-naturally occurring colloidal immobilization material capable of immobilizing and stabilizing the enzyme, the material being permeable to a compound smaller than the enzyme.

Yet another aspect is an enzyme immobilized in an acellular, colloidal immobilization material capable of immobilizing and stabilizing the enzyme, the material being permeable to a compound smaller than the enzyme.

A further aspect is an enzyme immobilized in a micellar or inverted micellar immobilization material capable of immobilizing and stabilizing the enzyme, the material being permeable to a compound smaller than the enzyme.

Another aspect is an enzyme immobilized in a cation-modified perfluoro sulfonic acid-PTFE copolymer capable of immobilizing and stabilizing the enzyme, the material being permeable to a compound smaller than the enzyme.

Yet another aspect is a biofuel cell comprising a bioanode and a cathode, wherein (a) the bioanode comprises a carbon cloth, a redox polymer film of polymethylene green, a salt-extracted tetrabutylammonium bromide-treated perfluorinated ion exchange polymer, and an alcohol dehydrogenase, (b) the alcohol dehydrogenase is incorporated within a micellar compartment of the salt-extracted tetrabutylammonium bromide treated perfluorinated ion exchange polymer, and (c) the redox polymer film of polymethylene green lies in apposition to the salt-extracted tetrabutylammonium bromide-treated perfluorinated ion exchange polymer and the carbon cloth.

A further aspect is a bioanode comprising a support membrane, redox polymer, quaternary ammonium salt-modified perfluorinated ion exchange polymer and a dehydrogenase, wherein (a) the dehydrogenase is incorporated within the quaternary ammonium salt-modified perfluorinated ion exchange polymer, and (b) the redox polymer is juxtaposed with the support membrane and the quaternary ammonium salt-modified perfluorinated ion exchange polymer.

Another aspect is a bioanode comprising a carbon cloth support membrane, a polymethylene green redox polymer, quaternary ammonium salt-modified perfluorinated ion exchange polymer and an alcohol dehydrogenase, wherein (a) the dehydrogenase is incorporated within the quaternary ammonium salt-modified Nafion® polymer, and (b) the redox polymer is juxtaposed with the carbon cloth support membrane and the quaternary ammonium salt-modified Nafion® polymer.

Yet another aspect is a perfluorinated ion exchange polymer comprising a modification and one or more enzymes, wherein the enzyme is incorporated within a micelle of the modified perfluorinated ion exchange polymer.

A further aspect is a method of generating electrical power, comprising oxidizing an organic fuel at an anode in the presence of a redox enzyme, which is incorporated in the anode, and reducing oxygen at a cathode, wherein (a) the anode comprises an ion conducting polymer, a redox polymer membrane and a supporting membrane (a) the redox enzyme is immobilized within the ion conducting polymer, (b) a cofactor is reduced during the oxidization reaction at the anode, (c) a redox polymer membrane catalyzes the oxidation of the reduced cofactor.

Another aspect of the invention is a method of generating electrical power, comprising oxidizing an alcohol at an anode and reducing oxygen at a cathode, wherein (a) the anode comprises a polymethylene green polymer, a quaternary ammonium bromide-treated Nafion® polymer, a carbon fiber supporting membrane and an alcohol dehydrogenase, (b) the alcohol dehydrogenase is immobilized within a micelle compartment of the quaternary ammonium bromide-treated Nafion® polymer, (c) a $NAD^+$ is reduced to NADH during the oxidization of the alcohol at the anode, and (d) the NADH is electro-oxidized to NAD+ at the polymethylene green polymer.

DETAILED DESCRIPTION

Figure 1:
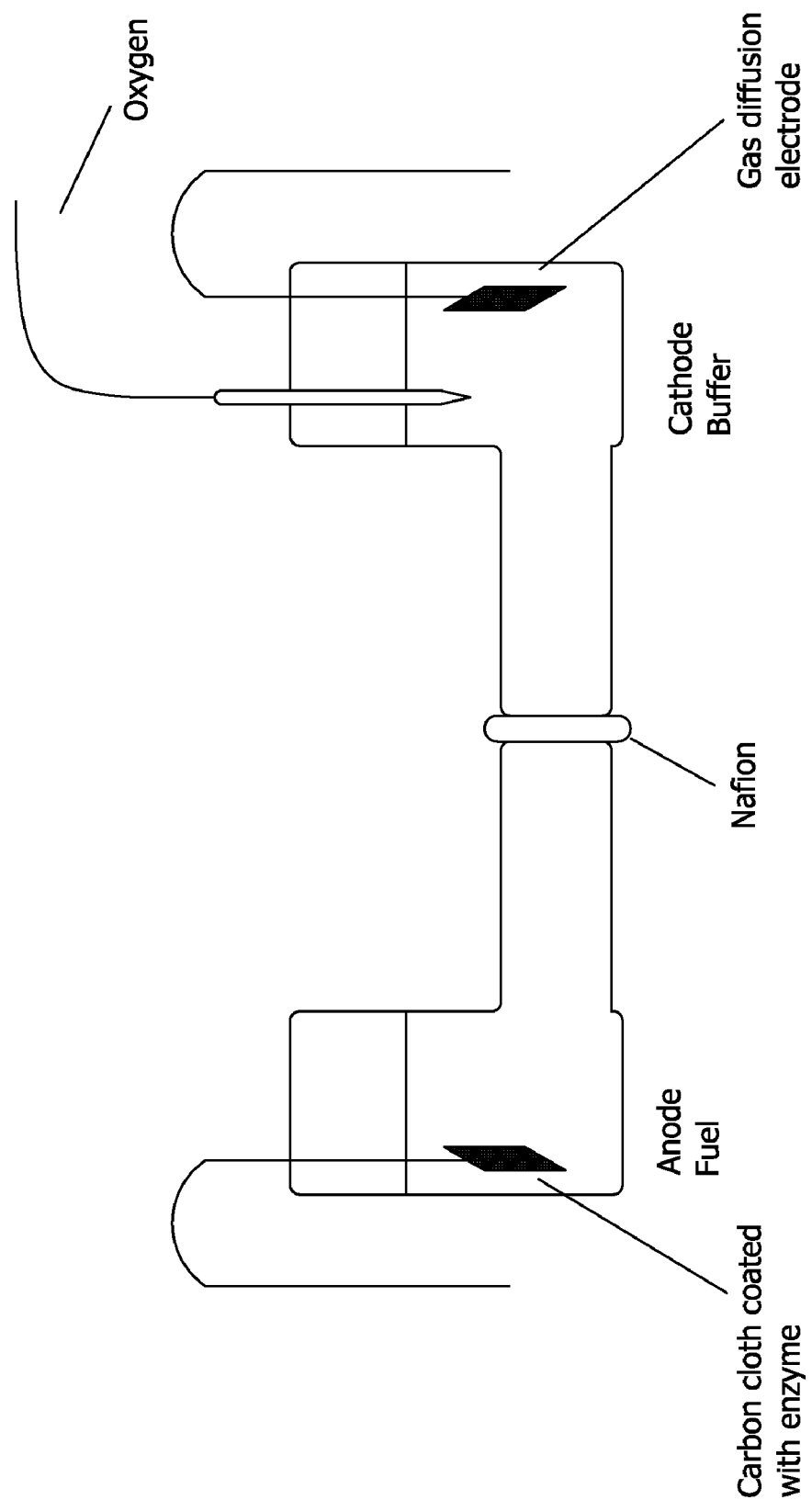
FIG. 1 is a schematic of the biofuel cell (Not to Scale).

Among the various aspects of the present invention is an immobilized enzyme for use in an application wherein increased enzyme stability is advantageous; particularly for use in biofuel cells and biosensors. The immobilization material forms a barrier that provides mechanical and chemical stability, and thus, stabilizes the enzyme for a longer period than previously known. For purposes of the present invention, an enzyme is "stabilized" if it retains at least about 75% of its initial catalytic activity for at least about 30 days to about 365 days. Another aspect among the various aspects of the present invention is a fuel cell, which utilizes organic fuels (or a fuel fluid comprising hydrogen, ammonia or a hydrocarbon) to produce electricity via enzyme mediated redox (oxidation/reduction) reactions. Another aspect of the invention is a biofuel cell comprising a bioanode and a cathode wherein the bioanode is separated from the cathode by an electrolyte. The bioanode comprises an enzyme immobilization material that is permeable to a fuel fluid, immobilizes the enzyme and stabilizes the enzyme. The stability of the immobilized enzyme allows the biofuel cell to produce at least about 75% of the initial current for at least about 30 days to about 365 days.

A. Enzyme Immobilization

Generally, an enzyme is immobilized in an immobilization material that immobilizes and stabilizes the enzyme. An enzyme immobilized within an immobilization material of the present invention can be utilized in a variety of applications. The enzymes and immobilization materials described below can be used in the applications of the present invention.

1. Enzyme

An enzyme is used to catalyze a desired reaction. Generally, naturally-occurring enzymes, man-made enzymes, artificial enzymes and modified naturally-occurring enzymes can be immobilized. In addition, engineered enzymes that have been engineered by natural or directed evolution can be used. Stated another way, an organic or inorganic molecule that mimics an enzyme's properties can be used in an embodiment of the present invention.

Exemplary enzymes are oxidoreductases.

2. Enzyme Immobilization Material

The enzyme is immobilized in an enzyme immobilization material. In one embodiment, the enzyme immobilization material is permeable to a compound that is smaller than the enzyme and immobilizes and stabilizes the enzyme. An immobilized enzyme is an enzyme that is physically confined in a certain region of the immobilization material while retaining its catalytic activity. There are a variety of methods for enzyme immobilization, including carrier-binding, cross-linking and entrapping. Carrier-binding is the binding of enzymes to water-insoluble carriers. Cross-linking is the intermolecular cross-linking of enzymes by bifunctional or multifunctional reagents. Entrapping is incorporating enzymes into the lattices of a semipermeable material. For example, the enzyme can be incorporated into a semipermeable gel or enclosed in a semipermeable polymer membrane. The particular method of enzyme immobilization is not critically important; however, the immobilization material (1) is permeable to the fuel fluid, (2) immobilizes the enzyme and (3) stabilizes the enzyme.

The immobilization material is permeable to a compound that is smaller than an enzyme. Stated another way, the immobilization material allows the movement of the compound that is smaller than an enzyme through it so the compound can contact the enzyme immobilized on or within the immobilization material. The immobilization material can be prepared in a manner such that it contains internal pores, channels, openings or a combination thereof, which allow the movement of the compound throughout the immobilization material, but constrain the enzyme to substantially the same space within the immobilization material.

The immobilization material will physically confine the enzyme substantially to a particular region of the material and allow the enzyme to retain its catalytic activity. In one embodiment, preferably, the enzyme is confined to a space that is substantially the same size and shape as the enzyme and the enzyme retains substantially all of its catalytic activity. The immobilization material contains pores, channels, openings or a combination thereof, where the pores, channels, openings or combination thereof, do not allow the enzyme to move substantially from its space, but they do allow a compound smaller than the enzyme to move through the immobilization material and contact the enzyme. The pores, channels or openings have physical dimensions that satisfy the above requirements and depend on the size and shape of the specific enzyme to be immobilized.

In one embodiment, preferably, the enzyme is located within a pore of the immobilization material and the fuel fluid travels in and out of the immobilization material through transport channels. The relative size of the pores and transport channels can be such that a pore is large enough to immobilize an enzyme, but the transport channels are too small for the enzyme to travel through them. In a further embodiment, preferably a transport channel has a diameter of at least about 10 nm. In still another embodiment, the ratio of the diameter of a pore to a transport channel is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more. In yet another embodiment, preferably, a transport channel has a diameter of at least about 10 nm and the ratio of the diameter of a pore to a transport channel is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more.

Moreover, the immobilization material stabilizes the enzyme. The immobilization material provides a chemical and mechanical barrier in order to stabilize the enzyme by protecting the enzyme from denaturation. Stated another way, the immobilization material buffers the enzyme environment and slows down enzyme denaturation. In addition, the immobilization material physically confines the enzyme and the physical confinement does not give the enzyme space to unfold; unfolding from a folded three-dimensional structure is a mechanism of enzyme denaturation. In one embodiment, the immobilization material, preferably, stabilizes the enzyme so that the enzyme retains its catalytic activity for at least about 30 days to about 365 days. The retention of catalytic activity is defined by the number of days that the enzyme retains at least about 75% of its initial activity. The enzyme activity can be measured by chemiluminescence, electrochemical, UV-Vis, radiochemical or fluorescence assay wherein the intensity of the property is measured at an initial time. The enzyme is considered to retain catalytic activity when the intensity is at least about 75% of the initial intensity. Typically, a fluorescence assay is used to measure the enzyme activity. A free enzyme in solution loses its catalytic activity within hours to a few days. Thus, the immobilization of the enzyme provides a significant advantage in stability. In another embodiment, preferably, the immobilized enzyme retains at least about 75% of its initial catalytic activity for at least about 30, 45, 60, 75, 90, 105, 120, 150, 180, 210, 240, 270, 300, 330, 365 days or more, preferably retaining at least about 80%, 85%, 90%, 95% or more of its initial catalytic activity for at least about 30, 45, 60, 75, 90, 105, 120, 150, 180, 210, 240, 270, 300, 330, 365 days or more.

In a further embodiment, the immobilization material is a non-naturally occurring colloidal material. In yet another embodiment, the immobilization material is an acellular colloidal material, such as a liposome. An acellular material is not made up of and does not contain cells. A colloidal material is a substance that consists of particles dispersed throughout another substance which are too small for resolution with an ordinary light microscope but are incapable of passing through a semipermeable membrane. In further embodiment, a colloidal material is a substance consisting of particles substantially larger than atoms or ordinary molecules but too small to be visible to the unaided eye. They can range in size from about $10^{-7}$ to $10^{-3}$ centimeters and are linked or bonded together in a variety of ways.

In another embodiment, the immobilization material has a micellar or inverted micellar structure. Generally, the molecules making up a micelle are amphipathic, meaning they contain a polar, hydrophilic group and a nonpolar, hydrophobic group. The molecules can aggregate to form a micelle, where the polar groups are on the surface of the aggregate and the hydrocarbon, nonpolar groups are sequestered inside the aggregate. Inverted micelles have the opposite orientation of polar groups and nonpolar groups. The amphipathic molecules making up the aggregate can arrange themselves in a variety of ways so long as the polar groups are in proximity to each other and the nonpolar groups are in proximity to each other. Also, the molecules can form a bilayer with the nonpolar groups pointing toward each other and the polar groups pointing away from each other. Alternatively, a bilayer can form wherein the polar groups can point toward each other in the bilayer, while the nonpolar groups point away from each other.

Generally, the micellar or inverted micellar immobilization material can be a polymer, a ceramic, a liposome or formed from other molecules that form a micellar or inverted micellar structure. Exemplary micellar or inverted micellar immobilization materials are perfluoro sulfonic acid-polytetrafluoro ethylene (PTFE) copolymer (or perfluorinated ion exchange polymer)(Nafion® or Flemion®), modified perfluoro sulfonic acid-polytetrafluoro ethylene (PTFE) copolymer (or modified perfluorinated ion exchange polymer)(modified Nafion® or modified Flemion®), polysulfone, micellar polymers, poly(ethylene oxide) based block copolymers, polymers formed from microemulsion and/or micellar polymerization and copolymers of alkyl methacrylates, alkyl acrylates and styrenes. Other exemplary micellar or inverted micellar immobilization materials are ceramics, sodium bis (2-ethylhexyl)sulfosuccinate, sodium dioctylsulfonsuccinate, lipids, phospholipids, sodium dodecyl sulfate, decyltrimethylammonium bromide, tetradecyltrimethylammonium bromide, (4-[(2-hydroxyl-1-naphthalenyl)azo]benzenesulfonic acid monosodium salt), linoleic acids, linolenic acids, colloids, liposomes and micelle networks.

In one embodiment, preferably, the micellar immobilization material is a modified perfluoro sulfonic acid-PTFE copolymer (or modified perfluorinated ion exchange polymer)(modified Nafion® or modified Flemion®) membrane. The perfluorinated ion exchange polymer membrane is modified with a hydrophobic cation that is larger than the ammonium ($NH_4^+$) ion. The hydrophobic cation functions in several ways. First, mixture-casting a perfluoro sulfonic acid-PTFE copolymer (or perfluorinated ion exchange polymer) with a hydrophobic cation to produce a modified perfluoro sulfonic acid-PTFE copolymer (or modified perfluorinated ion exchange polymer)(Nafion® or Flemion®) membrane provides an immobilization material wherein the pore size is dependent on the size of the hydrophobic cation. Accordingly, the larger the hydrophobic cation, the larger the pore size. This function of the hydrophobic cation allows the pore size to be made larger or smaller to fit a specific enzyme by varying the size of the hydrophobic cation.

In addition, the hydrophobic cation alters the properties of the perfluoro sulfonic acid-PTFE copolymer (or perfluorinated ion exchange polymer) membrane by exchanging the hydrophobic cation for protons as the counterion to the $-SO_3^-$ groups on the perfluoro sulfonic acid-PTFE copolymer (or perfluorinated ion exchange polymer) membrane. This change in counterion provides a buffering effect on the pH because the hydrophobic cation has a much greater affinity for the $-SO_3^-$ sites than protons do. This buffering effect of the membrane causes the pH of the pore to remain substantially unchanged with a change of pH of the solution. In addition, the membrane provides a mechanical barrier, which protects the enzymes immobilized in the membrane. Both the buffering effect and the mechanical barrier advantageously affect the stability of the enzymes immobilized in the modified perfluoro sulfonic acid-PTFE copolymer (or perfluorinated ion exchange polymer) membrane.

The following table demonstrates the buffering effect of the modified perfluoro sulfonic acid-PTFE copolymer membrane. The values represent the number of available exchange sites for protons per gram of modified perfluoro sulfonic acid-PTFE copolymer membrane; as the number of exchange sites available to protons decreases, the buffering capacity of the membrane toward the immobilized enzyme increases. The membrane abbreviations designate the following membranes: $NH_4Br$ is an ammonium bromide-modified Nafion® membrane, TMABr is a tetramethylammonium bromide-modified Nafion® membrane, TEABr is a tetraethylammonium bromide-modified Nafion® membrane, TpropABr is a tetrapropylammonium bromide-modified Nafion® membrane, TBABr is a tetrabutylammonium bromide-modified Nafion® membrane, and TpentABr is a tetrapentylammonium bromide-modified Nafion® membrane.

| Membrane | Mixture-Cast ($\times 10^{-6}$ mole/g) | Salt-Extracted ($\times 10^{-6}$ mole/g) |
|---|---|---|
| Nafion ® | 907 ± 68 | — |
| $NH_4Br$ | 521 ± 74 | 591 ± 95 |
| TMABr | 171 ± 19 | 458 ± 27 |
| TEABr | 157 ± 4 | 185 ± 22 |
| TPropABr | 133 ± 6 | 138 ± 77 |
| TBABr | 8.68 ± 2.12 | 96 ± 23 |
| TPentABr | 2.71 ± 0.6 | 1.78 ± 1.66 |

In order to prepare a modified perfluoro sulfonic acid-PTFE copolymer (or perfluorinated ion exchange polymer) membrane, the first step is to cast a suspension of perfluoro sulfonic acid-PTFE copolymer (or perfluorinated ion exchange polymer), particularly Nafion®, with a solution of the hydrophobic cations to form a membrane. After extracting the excess hydrophobic cations and their salts from the original membrane, the membrane is re-cast. Upon re-casting, the membrane contains the hydrophobic cations in association with the $-SO_3^-$ sites of the perfluoro sulfonic acid-PTFE copolymer (or perfluorinated ion exchange polymer) membrane.

In order to make more stable and reproducible quaternary ammonium salt-treated Nafion® membranes, the excess bromide salts must be removed from the casting solution. This salt-extracted membrane is formed by re-casting the mixture-cast membranes after the excess quaternary ammonium bromide and HBr salts have been extracted from the original membranes. Salt extraction of membranes retains the presence of the quaternary ammonium cations at the sulfonic acid exchange sites, but eliminates complications from excess salt that may be trapped in the pore or may cause voids in the equilibrated membrane. The chemical and physical properties of the salt-extracted membranes have been characterized by voltammetry, ion exchange capacity measurements, and fluorescence microscopy before enzyme immobilization [3].

Exemplary hydrophobic cations are ammonium-based cations, quaternary ammonium cations, alkyltrimethylammonium cations, alkyltriethylammonium cations, organic cations, phosphonium cations, triphenylphosphonium, pyridinium cations, imidazolium cations, hexdecylpyridinium, ethidium, viologens, methyl viologen, benzyl viologen, bis(triphenylphosphine)iminium, metal complexes, bipyridyl metal complexes, phenanthroline-based metal complexes, $[Ru(bipyridine)_3]^{2+}$ and $[Fe(phenanthroline)_3]^{3+}$.

In one embodiment, preferably, the hydrophobic cations are ammonium-based cations. In particular, the hydrophobic cations are quaternary ammonium cations. In another embodiment, the quaternary ammonium cations are represented by formula 1

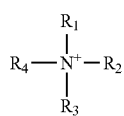

(1)

wherein $R_1$, $R_2$, $R_3$ and $R_4$ are independently hydrogen, hydrocarbyl, substituted hydrocarbyl or heterocyclo wherein at least one of $R_1$, $R_2$, $R_3$ and $R_4$ is other than hydrogen. In a further embodiment, preferably, $R_1$, $R_2$, $R_3$ and $R_4$ are independently hydrogen, methyl, ethyl, propyl, butyl, pentyl, hexyl, heptyl, octyl, nonyl or decyl wherein at least one of $R_1$, $R_2$, $R_3$ and $R_4$ is other than hydrogen. In still another embodiment, $R_1$, $R_2$, $R_3$ and $R_4$ are the same and are methyl, ethyl, propyl, butyl, pentyl or hexyl. In yet another embodiment, preferably, $R_1$, $R_2$, $R_3$ and $R_4$ are butyl.

Figure 5:
FIG. 5 is a fluorescence micrograph of annealed, alcohol dehydrogenase immobilized in a tetrabutylammonium bromide/Nafion® membrane that was treated with a $NAD^+$ and ethanol solution in pH 7.15 phosphate buffer.
Figure 6:
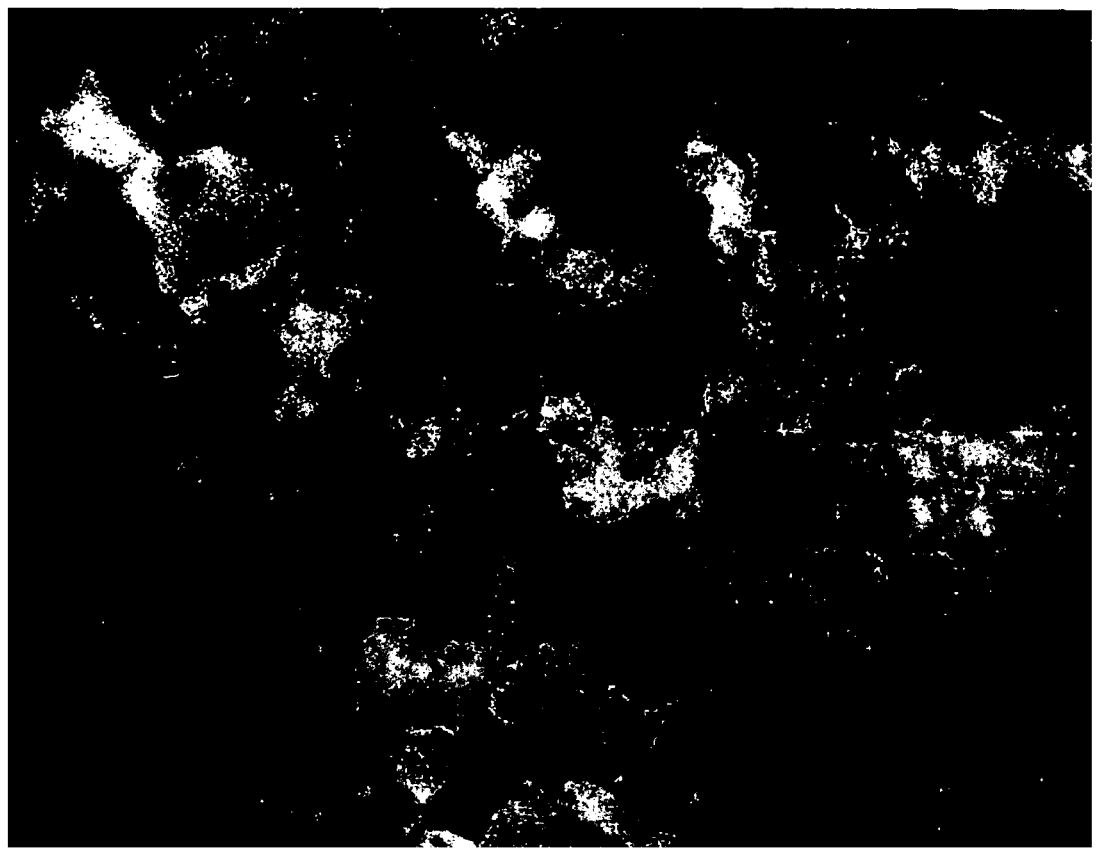
FIG. 6 is a fluorescence micrograph of aldehyde dehydrogenase immobilized in a tetrapentylammonium bromide/Nafion® membrane that was treated with a $NAD^+$ and acetaldehyde solution in pH 7.15 phosphate buffer.
Figure 7:
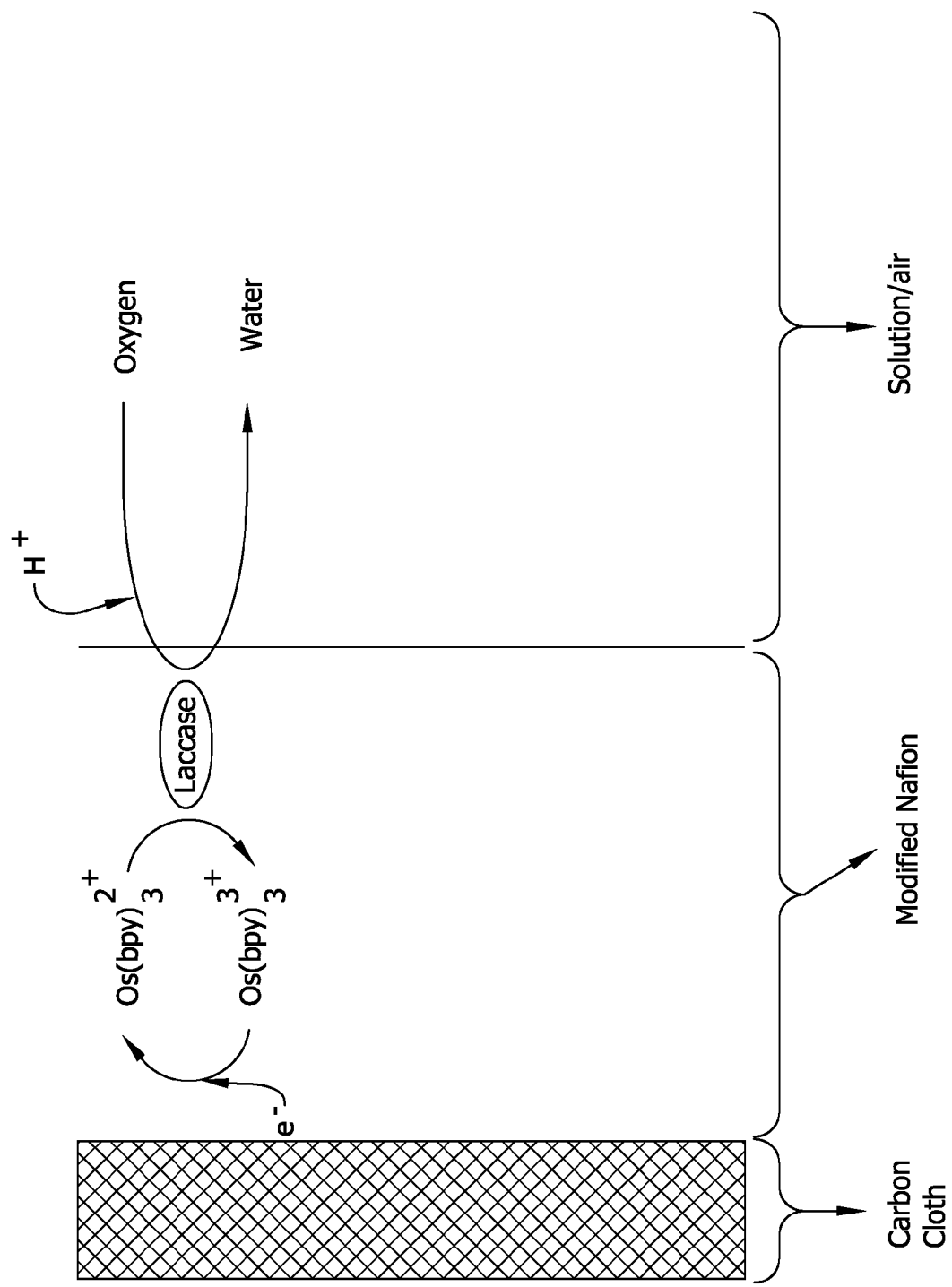
FIG. 7 is a schematic diagram of a biocathode using laccase immobilized in a Nafion® membrane.
Figure 8:
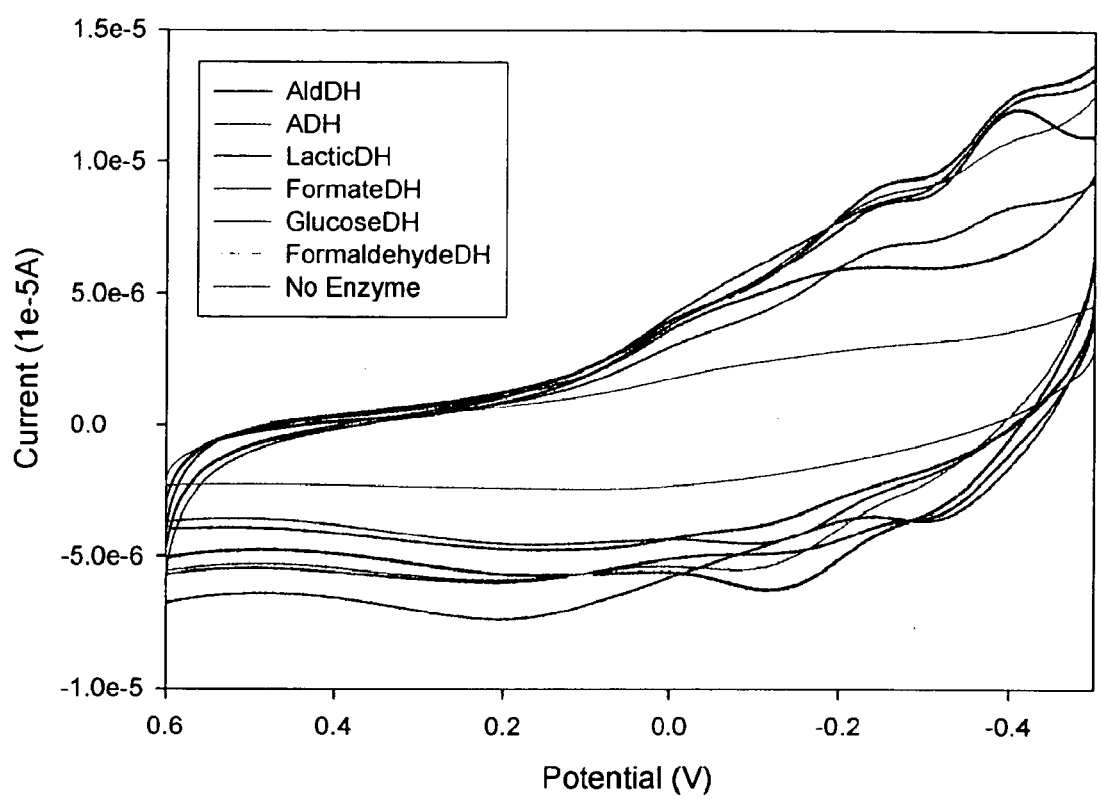
FIG. 8 is a cyclic voltammogram comparing fuels for tetrabutylammonium bromide/Nafion® membranes.
Figure 9:
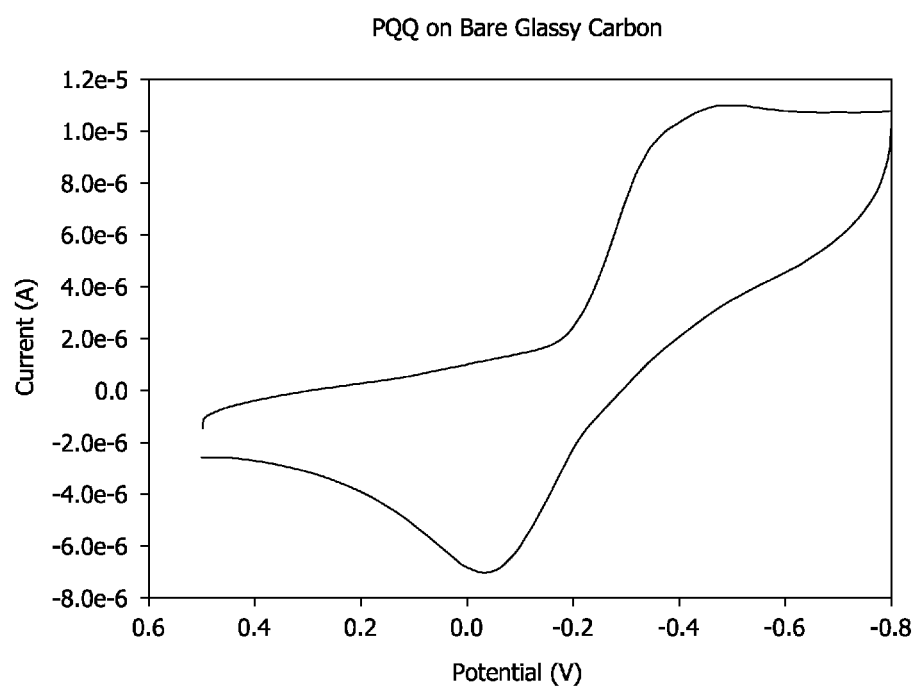
FIG. 9 is a cyclic voltammogram of pyrroloquinoline quinone (PQQ) on a bare glassy carbon electrode.

FIGS. 4-6 show fluorescence micrographs of enzymes immobilized in various modified perfluoro sulfonic acid-PTFE copolymer membranes that were treated with a $NAD^+$ and fuel fluid solution in pH 7.15 phosphate buffer. The fluorescence micrographs that show fluorescence indicate that the enzymes immobilized in the particular modified perfluoro sulfonic acid-PTFE copolymer membrane are still catalytically active enzymes after immobilization. This is one way to determine whether the particular immobilization material will immobilize and stabilize the enzyme while retaining the enzyme's catalytic activity.

Mixture-cast films of quaternary ammonium salts (such as: tetrabutylammonium bromide) and Nafion® have increased the mass transport of small analytes through the films and decreased the selectivity of the membrane against anions [2]. These membranes have very similar conductivities as unmodified Nafion, but they have a much higher preference to the quaternary ammonium bromide than to the proton, as shown by titrating the number of available exchange sites to protons in the membranes. Therefore, these films have similar electrical properties, but very different acid/base properties. The treated membranes maintain their neutral pH over a wide range of buffer pHs.

B. Biofuel Cell

Among the various aspects of the invention is a biofuel cell utilizing the immobilized enzyme described above. In a biofuel cell, the reaction that occurs at the anode is the oxidation of the fuel fluid with a concurrent release of electrons; the electrons are directed through an electrical connection to the cathode where an oxidant is reduced to water. The biofuel cell of the present invention provides an energy source (electricity) for an electrical load external to the biofuel cell. To facilitate the oxidation of the fuel fluid, the bioanode contains an electron conductor, an electrocatalyst (e.g., redox polymer) for an electron mediator (also know as cofactor) and an enzyme. The electron mediator is a compound that can accept electrons or donate electrons.

Initially, the oxidized form of the electron mediator reacts with the fuel fluid and the enzyme to produce the oxidized form of the fuel fluid and the reduced form of the electron mediator. Subsequently or concurrently, the reduced form of the electron mediator reacts with the oxidized form of the electrocatalyst to produce the oxidized form of the electron mediator and the reduced form of the electrocatalyst. The reduced form of the electrocatalyst is then oxidized at the anode and produces electrons to generate electricity. The redox reactions at the bioanode, except the oxidation of the fuel fluid, can be reversible, so the enzyme, electron mediator and electrocatalyst are not consumed. Optionally, the redox reactions can be irreversible if an electron mediator is added to provide additional reactant.

Alternatively, an electron conductor and an enzyme can be used wherein an electron mediator in contact with the bioanode is able to transfer electrons between its oxidized and reduced forms at unmodified carbon-based electrodes. If the electron mediator is able to transfer electrons between its oxidized and reduced forms at unmodified carbon-based electrodes, the subsequent reaction between the electrocatalyst and the electron mediator is not necessary and the electron mediator itself is oxidized at the anode to produce electrons and thus, electricity.

The biofuel cell of the present invention comprises a bioanode and a cathode. The release of electrons occurs at the bioanode and the reduction of an oxidant occurs at the cathode, wherein an electrical load is placed between the bioanode and the cathode.

1. Bioanode

Generally, the bioanode comprises elements that effect the oxidation of fuel fluid wherein electrons are released and directed to an external electrical load. An electrical load is a device that utilizes electricity. The external electrical load is in contact with a cathode where an oxidant is reduced. This flow of electrons from the fuel fluid to the components of the bioanode through an electrical connection to an electrical load and to a cathode provides a source of energy (electricity) for the electrical load.

In one embodiment, the bioanode comprises an electron conductor and an enzyme which is immobilized in an enzyme immobilization material. In another embodiment, the bioanode optionally further comprises an electrocatalyst for an electron mediator. An electrocatalyst can be absent from the bioanode when the bioanode contacts an electron mediator that is capable of undergoing a reversible redox reaction at the electron conductor. The above-identified components of the bioanode are adjacent to one another; meaning they are physically or chemically connected by appropriate means. In one embodiment, the components are physically and chemically connected by placement into a solution with an electrical connection between them. In a further embodiment, preferably, the components are physically connected by coating or otherwise depositing the individual components on the electron conductor. The components can be deposited separately, e.g. in layers, or they can be integrated into one deposition layer.

a. Electron Conductor

The electron conductor is a substance that conducts electrons. The electron conductor can be organic or inorganic in nature as long as it is able to conduct electrons through the material. The electron conductor can be a carbon-based material, a metallic conductor, a semiconductor, a metal oxide or a modified conductor.

Particularly suitable electron conductors are carbon-based materials. Exemplary carbon-based materials are carbon cloth, carbon paper, carbon screen printed electrodes, carbon paper (Toray), carbon paper (ELAT), carbon black (Vulcan XC-72, E-tek), carbon black, carbon powder, carbon fiber, single-walled carbon nanotubes, double-walled carbon nanotubes, multi-walled carbon nanotubes, carbon nanotube arrays, diamond-coated conductors, glassy carbon and mesoporous carbon. In addition, other exemplary carbon-based materials are graphite, uncompressed graphite worms, delaminated purified flake graphite (Superior® graphite), high performance graphite and carbon powders (Formula BT™, Superior® graphite), highly ordered pyrolytic graphite, pyrolytic graphite and polycrystalline graphite.

In a further embodiment, the electron conductor can be made of a metallic conductor; suitable electron conductors can be prepared from gold, platinum, iron, nickel, copper, silver, stainless steel, mercury, tungsten and other metals suitable for electrode construction. In addition, electron conductors which are metallic conductors can be constructed of nanoparticles made of cobalt, diamond and other suitable metals. Other metallic electron conductors can be silver-plated nickel screen printed electrodes.

In addition, the electron conductor can be a semiconductor. Suitable semiconductors are prepared from silicon and germanium, which can be doped with other elements. The semiconductors can be doped with phosphorus, boron, gallium, arsenic, indium or antimony, or a combination thereof.

Other electron conductors can be metal oxides, metal sulfides, main group compounds and materials modified with electron conductors. Exemplary electron conductors of this type are nanoporous titanium oxide, tin oxide coated glass, cerium oxide particles, molybdenum sulfide, boron nitride nanotubes, aerogels modified with a conductive material such as carbon, solgels modified with conductive material such as carbon, ruthenium carbon aerogels and mesoporous silicas modified with a conductive material such as carbon.

In another embodiment, the electron conductor has more than one component, wherein the first component can be carbon cloth wherein a second component can be an electron conductor disclosed above. The second electron conductor is attached to the carbon cloth and the aggregate of the two makes up the electron conductor.

In a further embodiment, the electron conductor is composed of uncompressed (GAT™ expanded, Superior Graphite Co.) graphite worms as described in section B.1.c. below.

b. Electron Mediators

The electron mediator is a compound that can accept or donate electron(s). Stated another way, the electron mediator has an oxidized form that can accept electron(s) to form the reduced form, wherein the reduced form can also donate electron(s) to produce the oxidized form. The electron mediator is a compound that can diffuse into the immobilization material and/or be incorporated into the immobilization material.

In one embodiment, the diffusion coefficient of the electron mediator is maximized. Stated another way, mass transport of the reduced form of the electron mediator is as fast as possible. A fast mass transport of the electron mediator allows for a greater circuit potential and power density of the biofuel cell in which it is employed.

Exemplary electron mediators are nicotinamide adenine dinucleotide ($NAD^+$), flavin adenine dinucleotide (FAD), nicotinamide adenine dinucleotide phosphate (NADP) or pyrroloquinoline quinone (PQQ) or equivalents of each. Other exemplary electron mediators are phenazine methosulfate, dichlorophenol indophenol, short chain ubiquinones and potassium ferricyanide.

In one embodiment, the electron mediator cannot under go a redox reaction at the electron conductor by itself. In this embodiment, the bioanode comprises an electrocatalyst for an electron mediator which facilitates the release of electrons at the electron conductor.

In another embodiment, a reversible redox couple that has a standard reduction potential of $0.0V\pm0.5$ V is used as the electron mediator. Accordingly, an electron mediator that provides reversible electrochemistry on the electron conductor surface can be used. The electron mediator is coupled with a naturally occurring enzyme that is dependent on that electron mediator, an enzyme modified to be dependent on that electron mediator or a synthetic enzyme that is dependent on that electron mediator. Examples of electron mediators that provide reversible electrochemistry on the electron conductor surface is pyrroloquinoline quinone (PQQ), phenazine methosulfate, dichlorophenol indophenol, short chain ubiquinones and potassium ferricyanide. In one embodiment, preferably, the electron mediator utilized with the bioanode is PQQ. Due to the capability of the electron mediator to provide reversible electrochemistry at the electron conductor surface, no electrocatalyst is necessary to catalyze the redox reaction of this type of electron mediator.

c. Electrocatalyst for an Electron Mediator

Generally, the electrocatalyst is a substance that facilitates the release of electrons at the electron conductor. Stated another way, the electrocatalyst improves the kinetics of a reduction or oxidation of an electron mediator so the electron mediator reduction or oxidation can occur at a lower standard reduction potential. The electrocatalyst can be reversibly oxidized at the anode to produce electrons and thus, electricity. When the electrocatalyst is adjacent to the electron conductor, the electrocatalyst and electron conductor are in electrical contact with each other, but not necessarily in physical contact with each other. In one embodiment, the electron conductor associates with or is adjacent to an electrocatalyst for an electron mediator.

Generally, the electrocatalyst can be an azine, a conducting polymer or an electroactive polymer. Exemplary electrocatalysts are methylene green, methylene blue, luminol, nitro-fluorenone derivatives, azines, osmium phenanthrolinedione, catechol-pendant terpyridine, toluene blue, cresyl blue, nile blue, neutral red, phenazine derivatives, tionin, azure A, azure B, toluidine blue O, acetophenone, metallophthalocyanines, nile blue A, modified transition metal ligands, 1,10-phenanthroline-5,6-dione, 1,10-phenanthroline-5,6-diol, [Re(phen-dione)$(CO)_3$Cl], [Re(phen-dione)$_3$]($PF_6$)$_2$, poly(metallophthalocyanine), poly(thionine), quinones, diimines, diaminobenzenes, diaminopyridines, phenothiazine, phenoxazine, toluidine blue, brilliant cresyl blue, 3,4-dihydroxybenzaldehyde, poly(acrylic acid), poly(azure 1), poly(nile blue A), poly(methylene green), poly(methylene blue), polyaniline, polypyridine, polypyrole, polythiophene, poly(thieno[3,4-b]thiophene), poly(3-hexylthiophene), poly(3,4-ethylenedioxypyrrole), poly(isothianaphthene), poly(3,4-ethylenedioxythiophene), poly(difluoroacetylene), poly(4-dicyanomethylene-4H-cyclopenta[2,1-b; 3,4-b'] dithiophene), poly(3-(4-fluorophenyl)thiophene) and poly(neutral red).

In a further embodiment, preferably, the electron conductor is composed of uncompressed graphite worms which were treated with an electrocatalyst for an electron mediator (or redox polymer), specifically methylene green, prior to fabrication and pressed into the desired shape by conventional means such as a hydraulic press. The pressing conditions for the electron conductor were optimized to produce a flexible material that was of sufficient thickness. After pressing of the electron conductor, the methylene green was polymerized by cyclic voltammetry in a solution of methylene green. After the electron conductor was washed and dried, the final material was attached to carbon cloth.

d. Enzyme

An enzyme is necessary to catalyze the oxidation of the fuel fluid. Generally, the enzymes described above can be used. Exemplary enzymes for use in a bioanode are oxidoreductases. In one embodiment, preferably, the oxidoreductases act on the CH—OH group or CH—NH group of donors.

In another embodiment, preferably, the enzyme is a dehydrogenase. In a further embodiment, the enzyme is alcohol dehydrogenase, aldehyde dehydrogenase, formate dehydrogenase, formaldehyde dehydrogenase, glucose dehydrogenase, glucose oxidase, lactatic dehydrogenase, lactose dehydrogenase or pyruvate dehydrogenase. In yet another embodiment, more preferably, the enzyme is an alcohol dehydrogenase. In still another embodiment, the enzyme is a PQQ-dependent dehydrogenase.

e. Enzyme Immobilization Material

An enzyme immobilization material is utilized in the biofuel cell. In one embodiment, the enzyme immobilization material is permeable to the fuel fluid and immobilizes and stabilizes the enzyme. The enzyme immobilization materials described above can be used in embodiments of the biofuel cell when they are permeable to the fuel fluid. The immobilization material is permeable to the fuel fluid so the oxidation reaction of the fuel can be catalyzed by the immobilized enzyme. Stated another way, the immobilization material allows the movement of the fuel fluid through it so the fuel can contact the enzyme immobilized on or within the immobilization material. The immobilization material can be prepared in a manner such that it contains internal pores, channels, openings or a combination thereof, which allow the movement of the fuel fluid throughout the immobilization material, but constrain the enzyme to substantially the same space within the immobilization material.

In another embodiment, preferably, the enzyme is located within a pore of the immobilization material and the fuel fluid travels in and out of the immobilization material through transport channels. The relative size of the pores and transport channels can be such that a pore is large enough to immobilize an enzyme, but the transport channels are too small for the enzyme to travel through them. In a further embodiment, preferably a transport channel has a diameter of at least about 10 nm. In still another embodiment, the ratio of the diameter of a pore to a transport channel is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more. In yet another embodiment, preferably a transport channel has a diameter of at least about 10 nm and the ratio of the diameter of a pore to a transport channel is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more.

f. Bioanode Embodiments

In a further embodiment, preferably, the bioanode is composed of an electron conductor that is modified by adsorption, polymerizing, or covalent bonding an electrocatalyst for an electron mediator onto the electron conductor. This embodiment has an advantage of increasing the surface area of the electron conductor. The treatment of the electron conductor by adsorbing an electrocatalyst on the surface of the electron conductor prior to fabrication and subsequent chemical or electrochemical polymerization of the electrocatalyst leads to higher catalytic activities compared to untreated electron conductors.

In another embodiment, more preferably, the bioanode is composed of an electron conductor composed of uncompressed graphite worms which were treated with methylene green prior to fabrication and pressed into the desired shape in a hydraulic press. After pressing of the electron conductor, the methylene green was polymerized by cyclic voltammetry in a solution of methylene green. After the electron conductor was washed and dried, the final material was attached to carbon cloth to complete the electron conductor. Subsequently, a perfluoro sulfonic acid-PTFE copolymer (or perfluorinated ion exchange polymer) membrane modified with tetrabutyl ammonium bromide (TBAB) to produce a TBAB-modified perfluoro sulfonic acid-PTFE copolymer (or TBAB-modified perfluorinated ion exchange polymer) membrane was prepared as described above and in the examples. An enzyme was added to the solution after re-casting. This TBAB-modified perfluoro sulfonic acid-PTFE copolymer (or TBAB-modified perfluorinated ion exchange polymer) membrane containing an immobilized enzyme was pipeted and/or painted onto the electron conductor and allowed to dry.

In one embodiment, preferably, the bioanode and cathode are fabricated into a membrane electrode assembly (MEA). In this embodiment, the cathode can be a traditional cathode, such as a platinum loaded (single or double sided loading) gas diffusion electrode, or a biocathode as described below. Generally, the cathode was laid down, a piece of perfluoro sulfonic acid-PTFE copolymer membrane was placed on top of the cathode and the bioanode was placed on top of the membrane. All the pieces were placed between the heating elements of a hydraulic press; pressure was applied so the top and bottom plates of the press began to touch, then the press was heated and finally, more pressure was applied. Alternatively, the MEA can be assembled as described above except that a few drops of liquid perfluoro sulfonic acid-PTFE copolymer membrane or modified perfluoro sulfonic acid-PTFE copolymer membrane were placed between both the bioanode and the piece of perfluoro sulfonic acid-PTFE copolymer membrane and the cathode and the piece of perfluoro sulfonic acid-PTFE copolymer membrane and pressed as above without heating.

In a further embodiment, the electron mediator can be physically bound to the enzyme. The physical bond can be a covalent or ionic bond between the electron mediator and the enzyme. In still another embodiment, if the electron mediator is capable of reversible electrochemistry at the electron conductor, the electron mediator can be physically bound to the enzyme and the electron mediator can also be physically bound to the electron conductor.

In still another embodiment, the electron mediator is immobilized in the immobilization material. In yet another embodiment, preferably, the oxidized $NAD^+$ is immobilized in a cation-modified perfluoro sulfonic acid-PTFE copolymer (cation-modified Nafion®) membrane. After the fuel fluid is added to the cell, the $NAD^+$ is reduced to NADH and the NADH can diffuse through the cation-modified perfluoro sulfonic acid-PTFE copolymer (cation-modified Nafion®) membrane.

In another embodiment, the present invention involves immobilizing dehydrogenase enzymes in salt-extracted tetrabutylammonium/perfluorinated ion exchange polymer membranes (e.g., Nafion® membranes or Flemion® membranes [Asahi Glass Co., Tokyo]). The salt-extracted polymer suspension is neutral and buffered enzyme solutions can be added to this suspension. The mixture can be cast onto an anode to form a modified electrode, wherein the enzyme is immobilized near the electrode's surface.

In another embodiment, the invention is drawn to a perfluorinated ion exchange polymer comprising a modification, which results in a neutral pH within the micelles of the polymer, and one or more enzymes, which is incorporated within a micelle of the modified perfluorinated ion exchange polymer. The preferred perfluorinated ion exchange polymer is a Nafion® polymer. Preferred enzymes are redox enzymes, such as dehydrogenases, which catalyze the oxidation of an organic fuel and the reduction of a cofactor. Cofactors include $NAD^+$, $NADP^+$ and FAD.

In one embodiment, the invention is drawn to a fuel cell comprising a bioanode and a cathode, wherein the bioanode comprises a redox polymer film, a modified ion exchange polymer membrane and a dehydrogenase. The dehydrogenase is incorporated within a micellar compartment of the modified ion exchange polymer membrane. Preferably, the modified ion exchange polymer membrane is a salt-extracted quaternary ammonium treated perfluorinated ion exchange polymer. Commercially available perfluorinated ion exchange polymers include Nafion® (DuPont) and Flemion® (Asahi Glass). Preferably, the perfluorinated ion exchange polymer is a Nafion® polymer or Flemion® polymer. Preferred quaternary ammonium salts include tetrabutylammonium bromide. A preferred redox polymer film is polymethylene green. The bioanode may comprise more than one different dehydrogenase, for example an alcohol dehydrogenase and an aldehyde dehydrogenase.

2. Fuel fluid

The fuel fluid is consumed in the oxidation reaction of the electron mediator and the immobilized enzyme. The fuel fluid's size is small enough so the diffusion coefficient through the immobilization material is large. Exemplary fuel fluids are hydrogen, ammonia, alcohols (such as methanol, ethanol, propanol, isobutanol, butanol and isopropanol), allyl alcohols, aryl alcohols, glycerol, propanediol, mannitol, glucuronate, aldehyde, carbohydrates (such as glucose, glucose-1, D-glucose, L-glucose, glucose-6-phosphate, lactate, lactate-6-phosphate, D-lactate, L-lactate, fructose, galactose-1, galactose, aldose, sorbose and mannose), glycerate, coenzyme A, acetyl Co-A, malate, isocitrate, formaldehyde, acetaldehyde, acetate, citrate, L-gluconate, beta-hydroxysteroid, alpha-hydroxysteroid, lactaldehyde, testosterone, gluconate, fatty acids, lipids, phosphoglycerate, retinal, estradiol, cyclopentanol, hexadecanol, long-chain alcohols, coniferyl-alcohol, cinnamyl-alcohol, formate, long-chain aldehydes, pyruvate, butanal, acyl-CoA, steroids, amino acids, flavin, NADH, $NADH_2$, NADPH, $NADPH_2$ and hydrogen.

In a further embodiment, preferably, the fuel fluid is an alcohol; more preferably, methanol and ethanol; particularly, ethanol.

3. Cathode

The cathode can be a traditional cathode or a biocathode. In a traditional cathode, the cathode is platinum-based, open to air and reduces an oxidant. If a traditional cathode is used, it is separated from the anode by a salt bridge. The salt bridge can take a variety of forms and be a material that allows ions to be transported between the anode and the cathode. In one embodiment, preferably, the salt bridge is a polymer electrolyte membrane (PEM).

In one embodiment, a fuel cell may comprise a bioanode as described (supra) and a biocathode, which comprises a second redox polymer film, a second modified ion exchange polymer membrane and an $O_2$-reductase. The second modified ion exchange polymer membrane may be a salt-extracted quaternary ammonium treated Nafion® polymer, the second redox polymer film may be a poly(N-vinyl-imidiazole), and the $O_2$-reductase may be a laccase. According to this embodiment, wherein the biofuel cell comprises both a bioanode and a biocathode, there is no need for a "salt-bridge", i.e., a PEM, to separate the anode from the cathode. This embodiment is particularly useful as a power source implantable in a biological host, such as a human.

4. Method for Generating Electricity

One of the various aspects of the present invention is a method of generating electrical power, using the bioanode of the present invention to oxidize an organic fuel (or a fuel fluid comprising hydrogen, ammonia or hydrocarbons), along with a cathode to reduce an oxidant such as oxygen or peroxide. In addition, another aspect of the invention is a method for generating electricity utilizing the bioanode and cathode described above, wherein an electrical load is placed between the bioanode and cathode wherein the bioanode, electrical load and cathode are connected with a conductive material. A fuel fluid is oxidized at the bioanode and an oxidant is reduced at the cathode. An electrical load is a device that uses electricity. In one embodiment, the bioanode is in contact with a solution containing the fuel fluid and the electron mediator and the cathode is in contact with a buffered solution. The solution contacting the bioanode is separated from the solution contacting the cathode by a salt bridge or PEM.

In another embodiment, the method of generating electrical power comprises the steps of oxidizing a fuel fluid at a bioanode and reducing an oxidant at a cathode, wherein (a) the bioanode comprises an electron conductor, an electrocatalyst for an electron mediator, and an enzyme which is immobilized in an enzyme immobilization material that is permeable to a fuel fluid and stabilizes the enzyme, (b) an oxidized form of an electron mediator is reduced during the oxidization of the fuel fluid at the bioanode, and (c) the reduced form of the electron mediator is oxidized by an electrocatalyst, subsequently or concurrently, the electrocatalyst is oxidized at the bioanode.

In yet another embodiment, the method of generating electrical power comprises the steps of oxidizing a fuel fluid at a bioanode and reducing an oxidant at a cathode, wherein (a) the bioanode comprises an electron conductor and an enzyme which is immobilized in an enzyme immobilization material that is permeable to a fuel fluid and stabilizes the enzyme, wherein an electron mediator capable of reversible electrochemistry at the electron conductor is present in a solution contacting the bioanode, (b) an oxidized form of the electron mediator is reduced during the oxidization of the fuel fluid at the bioanode, and (c) the electron mediator is oxidized at the bioanode.

In still another embodiment, the method of generating electrical power comprises the steps of oxidizing a fuel fluid at a bioanode and reducing an oxidant at a cathode, wherein (a) the bioanode comprises an electron conductor, an electrocatalyst for an electron mediator, and an enzyme which is immobilized in a micellar or inverted micellar enzyme immobilization material, (b) an oxidized form of an electron mediator is reduced during the oxidization of the fuel fluid at the bioanode, and (c) the reduced form of the electron mediator is oxidized by an electrocatalyst, subsequently the electrocatalyst is oxidized at the bioanode.

In a further embodiment, the method of generating electrical power comprises the steps of oxidizing a fuel fluid at a bioanode and reducing an oxidant at a cathode, wherein (a) the bioanode comprises an electron conductor and an enzyme which is immobilized in an enzyme immobilization material that is immobilized in a micellar or inverted micellar enzyme immobilization material, wherein an electron mediator capable of reversible electrochemistry at the electron conductor is present in a solution contacting the bioanode, (b) an oxidized form of the electron mediator is reduced during the oxidization of the fuel fluid at the bioanode, and (c) the electron mediator is oxidized at the bioanode.

In another embodiment, the invention is drawn to a method of generating electrical power, comprising oxidizing an organic fuel at an anode in the presence of a redox enzyme, which is incorporated in the anode; and reducing oxygen at a cathode. A preferred method of generating electrical power, comprises the steps of oxidizing an alcohol at an anode and reducing oxygen at a cathode, wherein (a) the anode comprises a polymethylene green polymer, a quaternary ammonium bromide-treated Nafion® polymer, a carbon fiber supporting membrane and an alcohol dehydrogenase; (b) the alcohol dehydrogenase is immobilized within a micelle compartment of the quaternary ammonium bromide-treated Nafion® polymer, (c) a $NAD^+$ is reduced to NADH during the oxidization of the alcohol at the anode, and (d) the NADH is electro-oxidized to $NAD^+$ at the polymethylene green polymer.

According to the present invention, biofuel cells were fabricated using dehydrogenase enzyme-immobilized ion conducting membranes that were cast on the surface of poly (methylene green)-modified anodes. In one embodiment of the invention, alcohol fuels are oxidized to aldehydes in the presence of alcohol dehydrogenase and $NAD^+$. The NADH product is the redox mediator for the fuel cell. Since NADH oxidation on platinum and carbon electrodes has poor reaction kinetics and occurs at large overpotentials [4], a polymer-based electrocatalyst was used to regenerate $NAD^+$ and to shuttle electrons from the NADH to the electrode. The electrocatalyst is preferably a poly(methylene green) [5].

Ethanol/$O_2$ biofuel cells employing these bioanodes, which incorporate aldehyde dehydrogenase in addition to alcohol dehydrogenase, have yielded power densities of 1.16 $mW/cm^2$ to 2.04 $mW/cm^2$, and open circuit potentials of 0.6 V to 0.82 V, depending on the ratio of alcohol dehydrogenase to aldehyde dehydrogenase in the polymer layer. Methanol/$O_2$ biofuel cells employing these bioanodes have yielded power densities of 1.55 $mW/cm^2$ and open circuit potentials of 0.71V.

In one embodiment of the present invention, incorporation of a redox enzyme in a modified ion-conducting polymer having a near neutral pH, allows for improved power densities of biofuel cells and increased longevity of bioanodes.

C. Enzyme Sensors

In a further embodiment, the immobilized enzymes of the invention can be used as sensors. Enzyme sensors are sensors where a chemical species to be measured (an analyte) undergoes an enzyme catalyzed reaction in the sensor before detection. The reaction between the analyte and the enzyme (for which the analyte should be a substrate) yields a secondary species; the concentration of the secondary species is proportional with or identical to the concentration of the analyte. The concentration of the secondary species is then detected either electrochemically or spectroscopically by a transducer, e.g., by means of an electrode or a fiber optic.

The enzyme of an enzyme sensor is typically included in a membrane suited for contacting the test fluid. In this case, the enzyme can be included as part of a membrane of a sensor or incorporated into the sensor proper, e.g. as part of a layer of an electrode. Hence, the analyte is contacted with the enzyme after diffusion into the outer part of the sensor, the enzyme/analyte reaction takes place, and the secondary species then diffuses to the detector part of the sensor. The immobilized enzyme in a micellar or inverted micellar immobilization material would have a suitable porosity so that the analyte could diffuse from the test fluid to the enzyme in a controlled manner, while retaining the enzyme in order to avoid leaching of the enzyme into the test fluid.

In one embodiment, a glassy carbon electrode was modified with methylene green and polymerized as described above. In addition, the glassy carbon electrode was coated with a tetrabutylammonium bromide modified perfluoro sulfonic acid-PTFE copolymer membrane in which alcohol dehydrogenase had been immobilized. The enzyme sensor detected ethanol.

D. Uses of Immobilized Enzymes

Generally, the immobilized enzymes of the present invention can be used in a variety of ways. Applications where it is advantageous that the enzyme is immobilized or stabilized are of particular interest.

In another embodiment, the immobilized enzymes are utilized in bioreactors and bioprocessing. Enzymes immobilized in an immobilization material, such as a micellar or inverted micellar immobilization material, serve to induce a chemical reaction of a substrate by catalysis. A substrate in accordance with the present invention is any substance for which the immobilized enzyme can catalyze a chemical reaction. Thus, a feed stream containing the substrate contacts the immobilized enzyme where the substrate reacts to form a product. In addition, the substrate is physically separated from the product as it passes through the immobilization material where the unreacted substrate is retained and passes through an exit end of a housing for separate collection.

The process using a bioreactor can be arranged as either a one-pass, continuous feed system or a recirculating system with the retained, unreacted substrate recirculated back into the feed stream and the product separately collected after passing through the immobilization material. The retained species and permeable species are physically separated generally by size as the smaller products pass through the immobilization material and the larger substrate is precluded from filtering through the immobilization material.

In yet another embodiment, the immobilized enzymes of the present invention are utilized in bioassays. Bioassay procedures involve the reaction of the test substance with an appropriate reagent, e.g., enzyme-substrate, or their converse reactions, together with direct or indirect quantitative measurement of the amount of reagent reacted by measurement of a characteristic of the reagent (or of another substance, an indicator, which has reacted with the reagent), such as color, radioactivity, or other physical characteristics. The test solution is brought into contact with the immobilized enzyme whereupon reaction occurs forming an immobilized complex. Radioactively labeled substrate is introduced and reacts at unoccupied sites. Determination of the radioactivity in the complex gives a measure of the amount of enzyme in the test sample.

In still another embodiment, the immobilized enzymes are used in enzyme therapy. Enzyme therapy consists of administration of enzymes to patients in a manner so the enzyme administered will catalyze the reactions in the body that the patient's own defective or deleted enzyme cannot. Immobilized enzymes are advantageous in this application due to the increased stability allowing the administered enzyme to remain active longer and thus, requiring less frequent treatment and a smaller dose of the enzyme.

In a further embodiment, the immobilized enzymes of the invention are utilized in immunoassays. One such assay is a qualitative enzyme linked immunosorbent assay (ELISA) in which color can be visually detected on the surface of filter paper, porous membrane, plastic paddle or other solid surfaces. This assay can be readily adapted to quantitative assays and to the use of other detectable signals besides color.

In another embodiment, the immobilized enzymes are used as biomimics. In a biomimic, synthetic systems are prepared that mimic biological or natural systems. For example, in order to mimic cellular systems or larger biological systems, such as the cardiovascular or endocrine system, the biomimic system would need to be able to selectively react with certain substances as well as release substances from the biomimic system. One way to selectively react and release substances is to use an immobilized enzyme that is immobilized in a semipermeable membrane. In this way, for example, the semipermeable membrane would mimic a cell membrane and the enzyme mediated reaction would mimic the many enzyme mediated reactions occurring in a natural system.

In a further embodiment, the immobilized enzymes are used in a system to mimic the Krebs cycle (or citric acid cycle). The Krebs cycle involves the oxidation of acetate or acetyl-CoA to carbon dioxide and water. A biomimic of the Krebs cycle would provide information about the factors affecting the energy producing cycle of cells. In addition, study of the Krebs cycle and its biomimics aids understanding of the important aspects for maximizing energy output using the biomimic.

DEFINITIONS

As used herein, a "fuel cell" comprises an anode and a cathode, which are separated to avoid an electrical short. Preferably, the anode and cathode are separated by a polymer electrolyte membrane. A biofuel cell utilizes a fuel fluid and an enzyme which catalyzes an oxidation of the fuel fluid. In one embodiment, a "biofuel cell" utilizes organic fuels as a source of energy and redox enzymes to catalyze the oxidation of the organic fuel. The terms "fuel cell" and "biofuel cell" are used interchangeably in throughout the instant disclosure. In one embodiment, the fuel cell of the instant invention may be used in applications that require an electrical supply, such as, but not limited to electronic devices and equipment, toys, internal medical devices, and electrically powered vehicles. In another embodiment, the fuel cell of the instant invention may be implanted into a living organism, wherein the organic fuel is derived from the organism and the fuel cell powers a device implanted in the living organism.

As used herein, the term "organic fuel" means any carbon-based compound that has stored energy. Organic fuels include but are not limited to nucleic acids, carbohydrates (such as glucose), alcohols, fatty acids and other hydrocarbons, ketones, aldehydes, amino acids and proteins. The organic fuel may be a biological compound within an organism. Preferred fuels are alcohols, which include methanol, ethanol, butanol, and isopropanol, and carbohydrates, especially glucose or polymers thereof. Preferred alcohols are ethanol and methanol.

The invention is also drawn to a bioanode. A bioanode is an anode comprising an enzyme that catalyzes the oxidation of a fuel fluid. In one embodiment, the term "bioanode" means an anode, which comprises a redox enzyme that catalyzes the oxidation of an organic fuel. An anode provides a source of electrons for an electrical circuit or electrical potential. In another embodiment, a preferred bioanode comprises a supporting membrane or structure, such as a carbon fiber cloth or sheet of carbon felt, which is juxtaposed to a redox polymer membrane, which is juxtaposed to an ion exchange polymer membrane. In one embodiment, the term "biocathode" means a cathode, which comprises a redox enzyme, such as a laccase, that catalyzes the reduction of oxygen.

As used herein, the term "redox polymer", "redox polymer film", or "redox polymer membrane" refers to a polymer capable of accepting or donating an electron from a compound, resulting in the oxidization or reduction, respectively, of the compound and the generation of a free electron available for transfer into an electric circuit. A preferred redox polymer is a polymethylene green, as described in reference 5 (Zou et al., 1996). Preferred compounds that are substrates for electrocatalysis by the redox polymer include reduced adenine dinucleotides, such as NADH, $FADH_2$ and NADPH. Redox polymer films useful for biocathodes include poly(N-vinyl-imidazole) and derivatives thereof.

As used herein, the term "support membrane" refers to a rigid or semi-rigid inert material capable of conducting an electric current and used to support the polymer membranes of a biofuel cell electrode. Support membranes may comprise any conducting material, such as for example stainless steel, stainless steel mesh, carbon, carbon nanotubes, platinum or semiconducting material. A preferred support membrane is a sheet of carbon felt. The terms "carbon felt", "carbon cloth" and "carbon cloth support membrane" are used interchangeably.

As used herein, the term "ion exchange polymer" or "ion exchange polymer membrane" refers to a polymer capable of allowing for the conduction of ions through it. A preferred ion exchange polymer is a perfluorinated ion exchange polymer, such as Nafion® (DuPont, Wilmington, Del.). The invention is also drawn to a perfluorinated ion exchange polymer, which comprises a modification, which includes quaternary ammonium ions at the sulfonic acid exchange sites. The modification results in a neutral pH within the micelles of the ion exchange polymer. According to the present invention, one or more redox enzymes are incorporated or trapped within the micelles (or "micellar compartment") of the salt-extracted quaternary ammonium treated perfluorinated ion exchange polymer.

In one embodiment, the term "enzyme" or "redox enzyme" refers to a protein that functions as a catalyst in a chemical reaction. Preferred enzymes include "dehydrogenases", which catalyze the oxidation of a fuel and the concomitant reduction of a "cofactor". Preferred cofactors include adenine dinucleotides, such as nicotinamide adenine dinucleotide ($NAD^+$), nicotinamide adenine dinucleotide phosphate ($NADP^+$) and flavin adenine dinucleotide (FAD). Dehydrogenases include alcohol dehydrogenases, aldehyde dehydrogenases, glyceraldehyde-3-phosphate dehydrogenase, formaldehyde dehydrogenase, formate dehydrogenase, lactate dehydrogenase, glucose dehydrogenase and pyruvate dehydrogenase. Redox enzymes useful for biocathodes include $O_2$ reductases, such as laccase.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The following examples illustrate the invention.

EXAMPLES

Example 1

Immobilized Enzymes

Casting solutions for making the mixture-cast membranes of Nafion® and quaternary ammonium bromides were prepared as discussed in Reference 2, which is herein incorporated by reference. One milliliter of the mixture-casting solution was placed in a weighing boat and allowed to dry. Previous studies have shown that all of the bromide ions that were introduced into a membrane were ejected from the membrane upon soaking that membrane in water [2]. Therefore, 7.0 mL of 18 MW water were added to the weighing boats and allowed to soak overnight. The water was removed and the films were rinsed thoroughly with 18 MW water and dried. The salt-extracted films were then resuspended in 1.0 mL of lower aliphatic alcohols.

Enzyme/Nafion® casting solutions with an enzyme to TBAB ratio of 2:1 (usually 1200 μL of 1.0 μM enzyme: 600 μL) and 0.03 g NAD⁺ were vortexed in preparation for coating on electrode. The solution was pipeted onto the electrode, allowed to soak into the carbon-felt electrode and dried.

Casting Solution Procedure

The following quaternary ammonium bromides were employed: ammonium bromide (Fisher), tetramethylammonium bromide (Aldrich), tetraethylammonium bromide (Fisher), tetrapropylammonium bromide (Aldrich), tetrabutylammonium bromide (Eastman), and tetrapentylammonium bromide (Aldrich).

Nafion® membranes incorporated with quaternary ammonium bromides were formed by co-casting the quaternary ammonium bromide with 5% by wt. Nafion® suspension (Solution Technologies, Inc.). The mixture-casting solutions were prepared by adding the quaternary ammonium bromides to the 5% by wt. suspension. All mixture-casting solutions were prepared so the concentration of quaternary ammonium bromides is in excess of the concentration of sulfonic acid sites in the Nafion® suspension. After optimization, it was determined that the most stable and reproducible membrane has a quaternary ammonium bromide concentration that is three times the concentration of the exchange sites.

One milliliter of the casting solution was placed in a weighing boat and allowed to dry. Previous studies had shown that all of the bromide ions that were introduced into a membrane were ejected from the membrane upon soaking that membrane in water. Therefore, 7.0 mL of 18 MW water were added to the weighing boats and allowed to soak overnight. The water was removed and the films were rinsed thoroughly with 18 MW water and dried. Then, the films were resuspended in 1.0 mL of methanol.

FIGS. 4-6 show fluorescence micrographs of enzymes immobilized in various modified perfluoro sulfonic acid-PTFE copolymer membranes that were treated with a NAD⁺ and fuel fluid solution in pH 7.15 phosphate buffer. The fluorescence micrographs that show fluorescence indicate that the enzyme immobilized in the particular modified perfluoro sulfonic acid-PTFE copolymer membrane are still catalytically active enzymes after immobilization. This is one way to determine whether the particular immobilization material will immobilize and stabilize the enzyme while retaining the enzyme's catalytic activity. The following Table details the enzymes and membranes that were prepared and whether the enzymes retained catalytic activity after immobilization. Where the table indicates "yes," the enzyme retained its catalytic activity after immobilization in the membrane and where the table indicates "no," the enzyme did not retain its catalytic activity after immobilization in the membrane.

| Membrane | Alcohol DH | Aldehyde DH | Formate DH | Glucose DH | Lactic DH | Formaldehyde DH |
|---|---|---|---|---|---|---|
| Nafion ® | No | No | No | No | No | No |
| AmmoniumBr | No | No | No | No | No | No |
| TMABr | No | No | No | No | No | No |
| TEABr | No | No | No | No | No | No |
| TPropABr | Yes | No | No | No | Yes | No |
| TBABr | Yes | Yes | Yes | Yes | Yes | Yes |
| TPentABr | No | Yes | Yes | Yes | Yes | No |

Example 2

Physical Cell Apparatus

The bioanodes of the present invention were tested on a physical test cell consisting of custom fabricated "U" shaped cylindrical glass tubing with 2.6 cm diameter, 14.8 cm height, and 7.6 cm length, as shown in FIG. 1. Approximately 50 mL of solution was contained on both sides of a Nafion® membrane (Aldrich). The cathode side of the test cell contained pH 7.15 phosphate buffer solution saturated with dissolved oxygen bubbled in via external source (AirGas). The cathode material is an ELAT electrode with 20% Platinum on Vulcan XC-72 (E-Tek). The anode side of the test cell was filled with pH 7.15 buffer containing 1.0 mM NAD⁺ and 1.0 mM fuel (ethanol or methanol). The bioanode of the instant invention, comprising enzyme, served as the anode. The complete cell was allowed to equilibrate for 2-6 hours before data collection. All data were collected and analyzed for the test cell with a CH Instruments 810 potentiostat interfaced to a PC computer. Each type of biofuel cell was tested in triplicate and all reported uncertainties correspond to one standard deviation.

Example 3

Bioanodes for Ethanol

Figure 2:
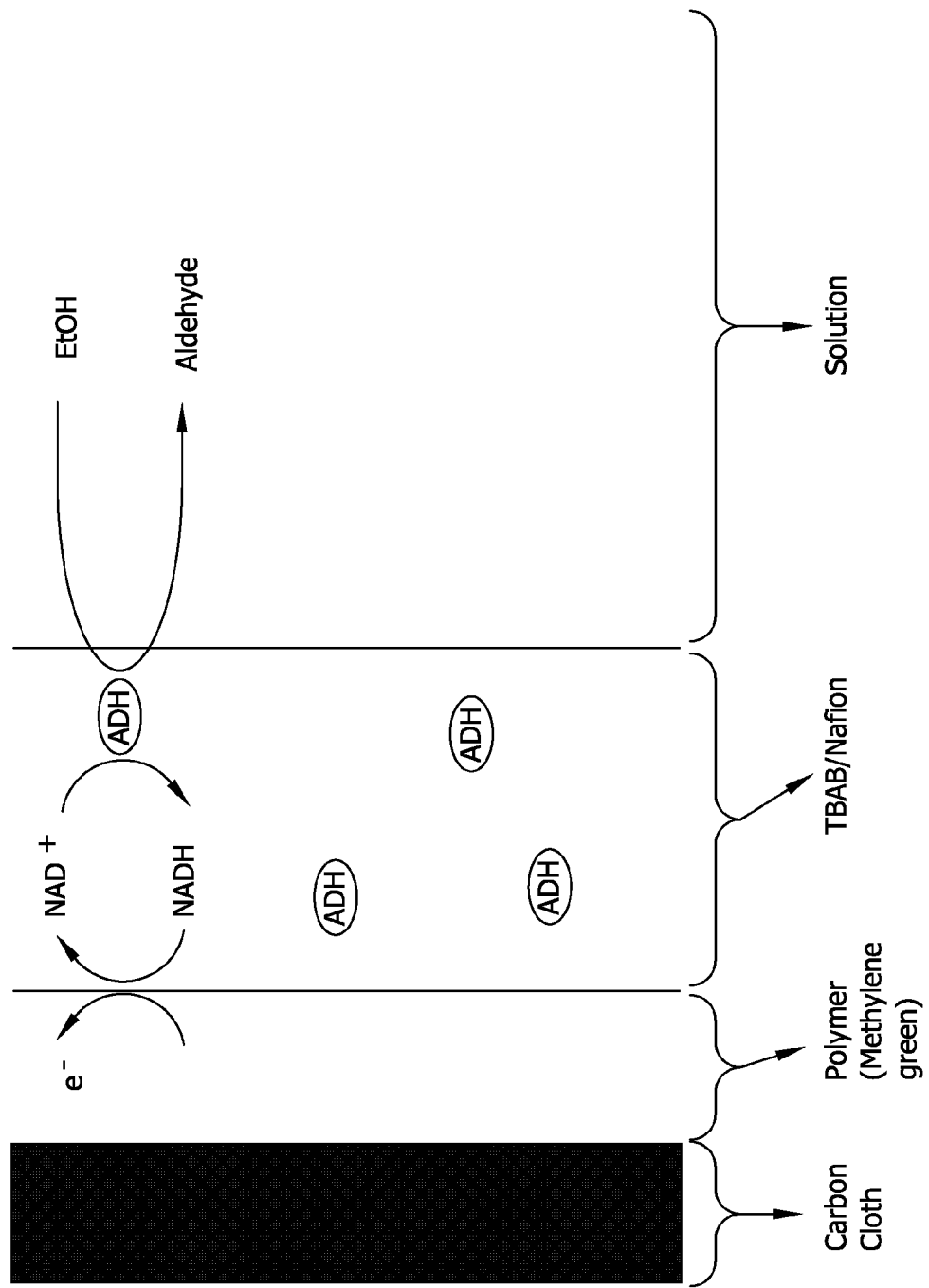
FIG. 2 is a schematic of the oxidation of ethanol to aldehyde is catalyzed by $NAD^+$-dependent alcohol dehydrogenase (ADH). NADH is electrolyzed at a poly(methylene green)-modified electrode.

Bioanodes for ethanol were designed as shown in FIG. 2. These bioanodes have NAD⁺ and either alcohol dehydrogenase or a mixture of alcohol dehydrogenase and aldehyde dehydrogenase immobilized in a salt-extracted tetrabutylammonium ("TBAB")/Nafion® membrane. The membrane is cast on a poly(methylene green)-modified carbon cloth electrode. These bioanodes can function for greater than 30 days, where functioning is determined by power outputs that are greater than 20% of the initial power output of the fuel cell.

Figure 3:
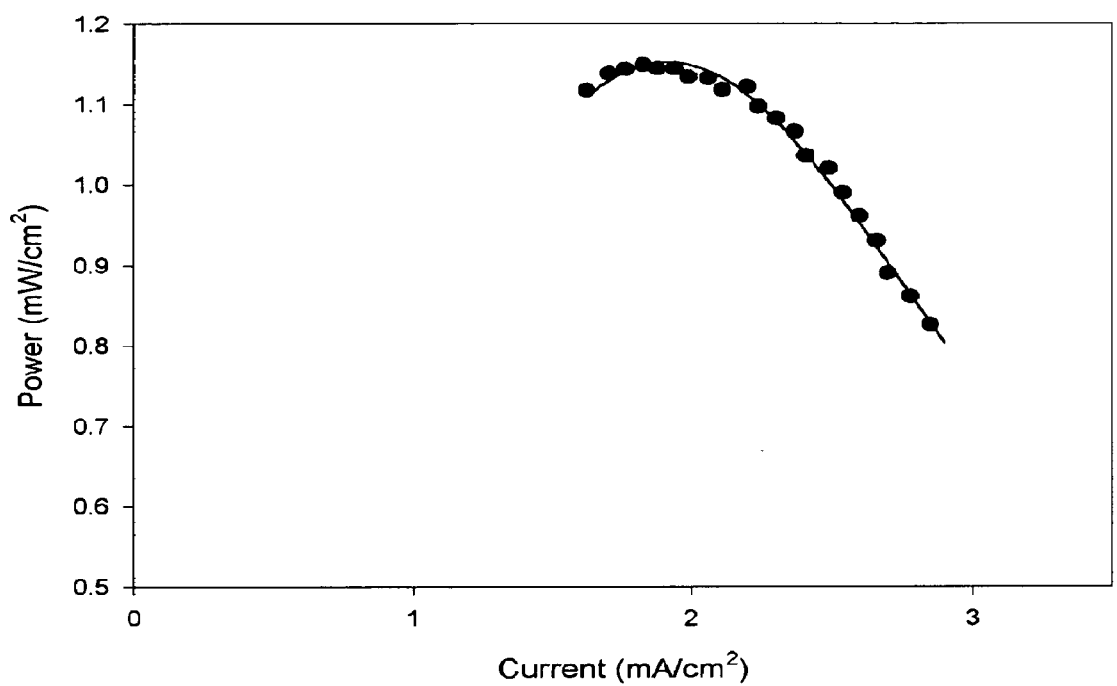
FIG. 3 is a representative power curve for an ethanol/$O_2$ biofuel cell at room temperature with an open circuit voltage of 0.60V.
Figure 4A:
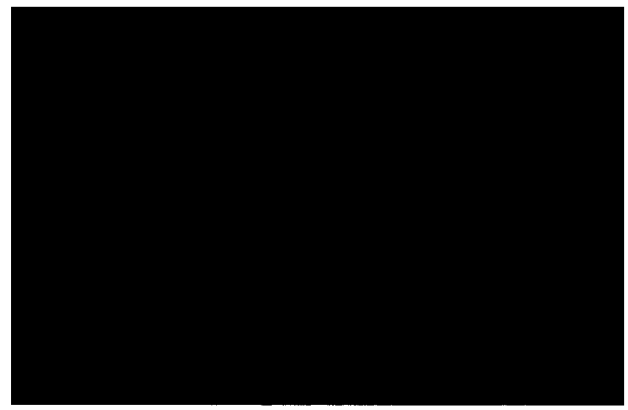
FIG. 4 is a series of fluorescence micrographs of the formation of NADH at alcohol dehydrogenase immobilized in a modified Nafion® membranes that were treated with $NAD^+$ and ethanol in a pH 7.15 phosphate buffer where (a) is an unmodified Nafion® membrane, (b) is a tetramethylammonium bromide/Nafion® membrane, (c) is a tetraethylammonium bromide/Nafion® membrane, (d) is a tetrapropylammonium bromide/Nafion® membrane, (e) is a tetrabutylammonium bromide/Nafion® membrane, and (f) is a tetrapentylammonium bromide/Nafion® membrane.
Figure 4B:
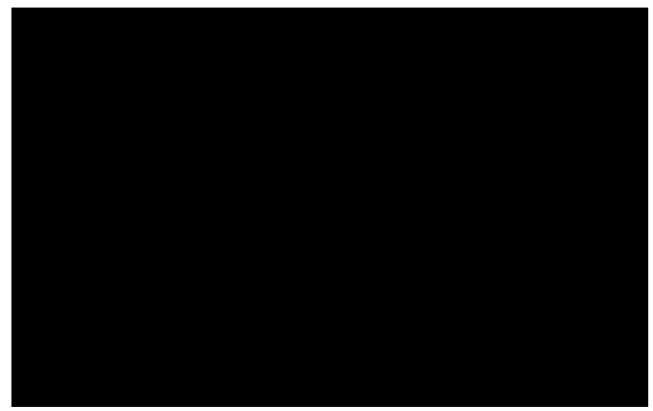
Figure 4C:
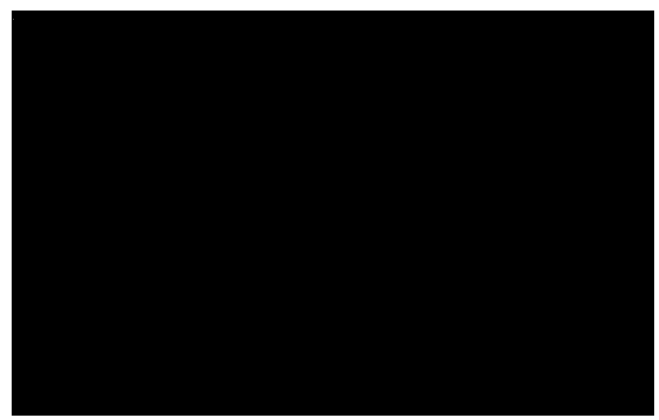
Figure 4D:
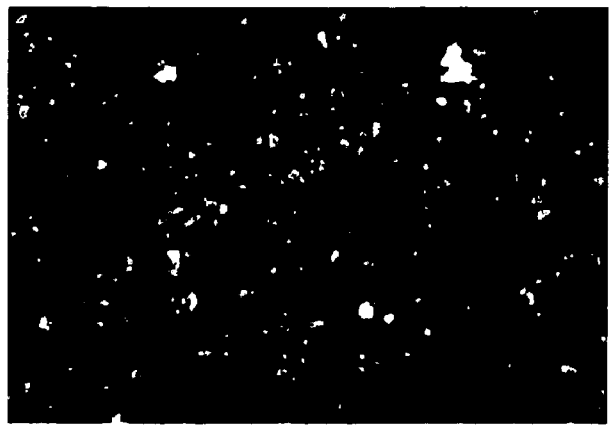
Figure 4E:
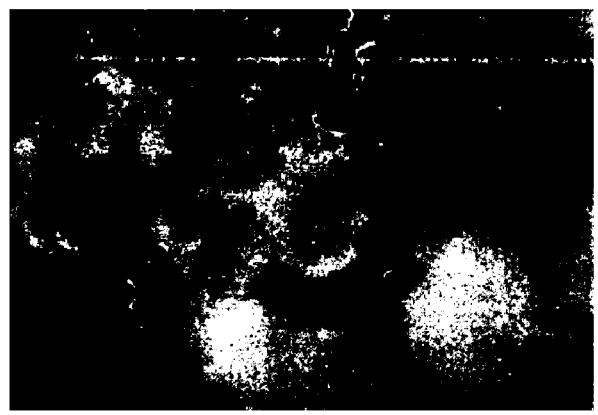
Figure 4F:
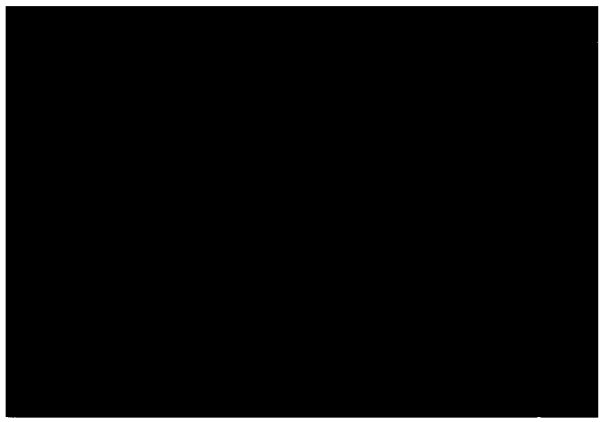

Bioanodes employing alcohol dehydrogenase immobilized in a TBAB/Nafion® membrane have shown open circuit potentials ranging from 0.60 to 0.62 V at 20° C. and a buffer pH of 7.15. The average maximum power density for the ethanol-based biofuel cell is 1.16±0.05 mW/cm². A representative power curve for the ethanol/$O_2$ fuel cell is shown in FIG. 3. The bioanode tested in FIG. 3 has $1.2 \times 10^{-9}$ moles of alcohol dehydrogenase enzyme immobilized in the TBAB/Nafion® membrane. A pH 7.15 phosphate buffer was chosen because the poly(methylene green) electrocatalyst has the highest catalytic efficiency for the oxidation of NADH at a neutral pH [5], even though the optimal pH for the enzyme is 8.6-9.0 [7]. This power curve was taken after 2 days. The maximum power decreased 6.1% over the first 7 days.

Bioanodes employing mixtures of alcohol dehydrogenase and aldehyde dehydrogenase immobilized in TBAB/Nafion® membranes have been fabricated and tested. This bioanode employed $1.2 \times 10^{-9}$ moles of alcohol dehydrogenase and $1.2 \times 10^{-9}$ moles of aldehyde dehydrogenase immobilized in the TBAB/Nafion® membrane. The open circuit potential of the ethanol/$O_2$ fuel cells employing alcohol dehydrogenase and aldehyde dehydrogenase is 0.82V. The maximum power density for the ethanol-based biofuel cells with a equal molar mixture of alcohol dehydrogenase and aldehyde dehydrogenase is 2.04 mW/cm².

In order to compare these alcohol/$O_2$ biofuel cells to biofuel cells in literature, a methanol/$O_2$ biofuel cell was fabricated and tested. The methanol bioanode had $1.2 \times 10^{-9}$ moles of alcohol dehydrogenase, $1.2 \times 10^{-9}$ moles of formaldehyde dehydrogenase, and $1.2 \times 10^{-9}$ moles of formate dehydrogenase immobilized in the TBAB/Nafion® membrane. The alcohol dehydrogenase oxidizes methanol to formaldehyde, which is subsequently oxidized to formate by formaldehyde dehydrogenase. Finally, formate is oxidized to carbon dioxide by formate dehydrogenase, thereby, forming 3 moles of NADH for each mole of fuel reacted.

The methanol-based biofuel cells presently in the art have open-circuit potentials ranging from 0.64 to 0.71V at 20° C. and a buffer pH of 7.15. The average maximum power density for the methanol-based biofuel cell is 1.55±0.19 mW/cm². The state of the art methanol/$O_2$ biofuel cell developed by Whitesides and coworkers had an open circuit potential of 0.8 V and a maximum power output of the cell of 0.67 mW/cm² [8]. The methanol biofuel cell described in Reference 1 did not have immobilized enzyme, so the lifetime of the fuel cell is limited to a few days at most. The TBAB/Nafion® membrane-based methanol biofuel cells of the present invention have been tested for greater than 5 days with no degradation in performance.

Although there are a number of other methanol biofuel cells in the literature [9-11], the highest reported open circuit potential is 0.3 V. This is due to a combination of poor redox mediators and poor catalytic activity. The poly(methylene green) redox mediator exhibits higher stability than aqueous redox mediators or adsorbed redox mediators and reduces the oxidation overpotential of NADH by 400 mV [5] and the TBAB/Nafion® membrane provides an ideal environment for enzyme immobilization.

Example 4

Reagents and Electrode Preparation

Methylene green (Sigma), sodium nitrate (Fisher), sodium borate (Fisher), Nafion® 1100 suspension (Aldrich) and Nafion® 117 (Aldrich) were purchased and used as received. Enzymes employed include alcohol dehydrogenase (E.C. 1.1.1.1, initial activity of 300-500 Units/mg), aldehyde dehydrogenase (E.C. 1.2.1.5, initial activity of 2-10 Units/mg), formaldehyde dehydrogenase (E.C. 1.2.1.2, initial activity of 1-6 Units/mg), and formate dehydrogenase (E.C. 1.2.1.46, initial activity of 5-15 Units/mg). Enzymes were purchased from Sigma (St. Louis, Mo.) and Roche Applied Science (Indianapolis, Ind.), stored at 0° C., and used as received. Additionally, $NAD^+$ and NADH were purchased from Sigma and used as received.

The bioanode consists of 1 cm×1 cm square carbon felt (Alfa Aesar) electropolymerized with the methylene green. A thin film of poly(methylene green) was formed by performing cyclic voltammetry using a CH Instruments 810 or 620 potentiostat (Austin, Tex.) from −0.3 Volts to 1.3 Volts for 12 sweep segments at a scan rate of 0.05 V/s in a solution containing 0.4 mM methylene green and 0.1 M sodium nitrate in 10 mM sodium tetraborate. The electrode was rinsed and then allowed to dry overnight before further modification.

Examples 5-7

Bioanodes for Various Fuel Fluids

The same procedure as used in Example 3 except the designated enzyme and fuel fluid were used.

| Example # | Fuel fluid | Enzyme | Membrane | Cofactor | Max. Power |
|---|---|---|---|---|---|
| 5 | propanol | alcohol dehydrogenase | TBAB/ Nafion ® | NAD⁺ | 0.808 mW/cm² |
| 6 | glucose | glucose dehydrogenase | TBAB/ Nafion ® | NAD⁺ | 0.39 mW/cm² |
| 7 | mysteric acid | Co-Enzyme A | TBAB/ Nafion ® | FAD | 0.63 mW/cm² |

Example 8

Graphite Worms Treated w/Polymethylene Green

Methylene green (Sigma), sodium nitrate (Fisher), sodium borate (Fisher) were purchased and used as received. GAT expanded graphite worms, lab code: 3-96-16 (Superior Graphite Co.), carbon cloth with no wet proofing (E-Tek), and carbon tape (Spi Supplies), were used as received.

A buffer containing the methylene green was prepared in 18 MW water by adding 1 mM concentrations of methylene green, sodium nitrate, and sodium borate. The solutes were sufficiently dissolved before use. The desired amount of GAT expanded graphite worms were then placed in a large container which was filled with the appropriate amount of methylene green buffer solution. The graphite and methylene green buffer solution was thoroughly mixed for up to 30 minutes to ensure complete adsorption of the methylene green to the surface of the graphite.

The mixture of graphite and buffer solution was allowed to separate based on the low density of the graphite in the solution. The excess buffer was then poured off of the graphite which was then washed with 18 MW water. After each washing, the solution was allowed to separate, excess poured off, and additional washings were performed. This process was repeated until the washing solution was clear and no longer appeared to contain excess methylene green. The final washing liquid was poured off and the now pre-treated graphite material was allowed to dry completely before further use.

The resulting material resembled a loose graphite powder which required fabricating into a usable electrode form. There was extreme flexibility in fabricating a final electrode in any desired dimensions or shapes. The chosen parameters were to prepare a 2.5 cm×2.5 cm electrode. This was accomplished by filling a custom fabricated plexi glass mold of the desired dimensions with the pre-treated graphite material. The material was pressed with a hydraulic jack to varying pressures. Typically, 3000 psi was used.

Anything less than 3000 psi pressing of the worms resulted in a mechanically unstable electron conductor. Typically, electron conductors were pressed to 3000-4000 psi. This resulted in an electron conductor that was mechanically stable enough to be used without additional support such as adhering it to carbon fiber. Additionally, these pressing conditions yielded an electron conductor that was semi-permeable to liquid. Higher pressures produced an electron conductor so compact, that liquids will not readily absorb into the electron conductor.

The resulting electrode was rugged and able to be attached to a support material for further stability. The support material used was carbon cloth. A layer of double-sided carbon tape was adhered to one side of the carbon cloth on top of which was placed the pre-treated pressed graphite worms.

Polymerization of the redox species was carried out at this point to improve the stability and longevity of the redox species. The polymerization can be accomplished by chemical or electrochemical means. In this instance, the redox species was polymerized electrochemically by placing the fabricated electrode in a solution containing 1 mM methylene green, 1 mM sodium nitrate and 1 mM sodium borate. The system was interfaced to a CH Instruments 810 potentiostat with the fabricated electrode acting a the working electrode, a platinum counter electrode and a Ag/AgCl reference. The potential was scanned from −0.3 to 1.3 and back to −0.3 V for 14 sweep segments. This resulted in a stable methylene green polymer on the electrode.

Example 9

Biocathode

Immobilizing oxidase, particularly laccase, enzymes in quaternary ammonium doped Nafion® films is similar to immobilizing dehydrogenase enzymes. A series of quaternary ammonium salts will be employed to determine which salt gives optimal enzyme activity when the enzyme is immobilized. The enzymes typically employ oxygen as the oxidant. The enzyme activity will be determined electrochemically (cyclic voltammetry) in a saturated oxygen environment in variety of buffers with differing pH ranges, but a redox mediator will be necessary due to the poor electrochemistry of peroxide at most electrode materials. Redox mediators that will be tested include $[Fe(bipyridine)_3]^{2+}$, $[Os(bipyridine)_3]^{2+}$, $[Ru(bipyridine)_3]^{2+}$ and any other redox couples that are physically stable and have reversible electrochemistry and have standard reduction potentials between 0.8 V and 2.0 V. This redox mediator can be mixture-cast with the membrane, salt-extracted into the membrane before final casting, or extracted into the membrane after casting.

Example 10

Membrane Electrode Anode (MEA)

The Membrane Electrode Assembly (MEA) process began with construction of the bioanode. The bioanode can be constructed out of any previously mentioned carbon, graphite, or metal electrode material. The overall MEA process remains unchanged.

When using methylene green pre-treated uncompressed graphite worms, the electrode was prepared as previously described. After the electrode was pressed under hydraulic pressure to desired specifications, electropolymerized with methylene green, coated with the modified Nafion®/enzyme/coenzyme polymer, and allowed to dry it was ready for use in the MEA. The electrode was typically coated on both sides with the Nafion®/enzyme/coenzyme polymer.

The process for preparation of an MEA included, first, cleaning and laying down a piece of Kapton (DuPont). The Kapton served to keep the MEA from sticking to the heat press, and it also kept the MEA clean. A platinum loaded (single or double sided loading) gas diffusion electrode (Etek) was placed on the piece of Kapton over which was laid a piece of Nafion® 117, 112, or 111 that was cut approximately 2.5 times larger than the gas diffusion electrode. Next, the previously prepared bioanode was placed on top of the Nafion® membrane. The assembly was slightly wetted before placing another piece of Kapton on top of the bioanode to hold the assembly together.

The MEA assembly was then placed between the heating elements of a hydraulic press. Only enough pressure was applied so that the top and bottom platens of the press just began to touch. The heat was turned on and the platens are allowed to heat to 120-135° C. Once they reach temperature, pressure was applied to desired specifications, typically 3000-4000 psi. The platens can be pre-heated before placing the MEA assembly in the press. The procedure does not necessarily have to follow these steps exactly; it can be modified and still be successful.

After being under pressure for 3-5 minutes the MEA was removed and allowed to cool before separating it from the Kapton.

It is possible to create an MEA without heat pressing. The MEA was assembled identically except that a few drops of liquid Nafion® or salt modified Nafion® was placed between both the anode and Nafion® 117, 112, or 111 and the cathode and Nafion® 117, 112, or 111. This assembly was then pressed, without heat, until the liquid Nafion® has dried.

Additionally, the anode can be pre-prepared in the following fashion. The desired electrode material was electropolymerized or chemically polymerized with the redox polymer if a redox polymer is required. At this point the electrode was placed in the MEA assembly, without enzyme on it, and heat pressed as described above. After pressing and cooling, the enzyme was cast on the anode side of the completed MEA.

Example 11

PQQ Dependent Enzyme

An example of a coenzyme that can be oxidized at an unmodified electrode is pyrroloquinoline quinone (PQQ). PQQ was discovered as a redox cofactor in bacterial alcohol dehydrogenases. PQQ contains an o-quinone moiety that exhibits an efficient, pH-dependent and reversible electron transfer between its oxidized and reduced forms at unmodified carbon-based electrodes. Utilizing PQQ dependent dehydrogenase enzymes allows for the elimination of electrocatalyst for use in biofuel cells and sensors. This simplifies electrode setup, decreases cost, and results in less power loss from slow mass transport due to PQQ's higher flux through the membrane because of the smaller size of the molecule.

Example 12

Enzyme Sensor

Figure 10:
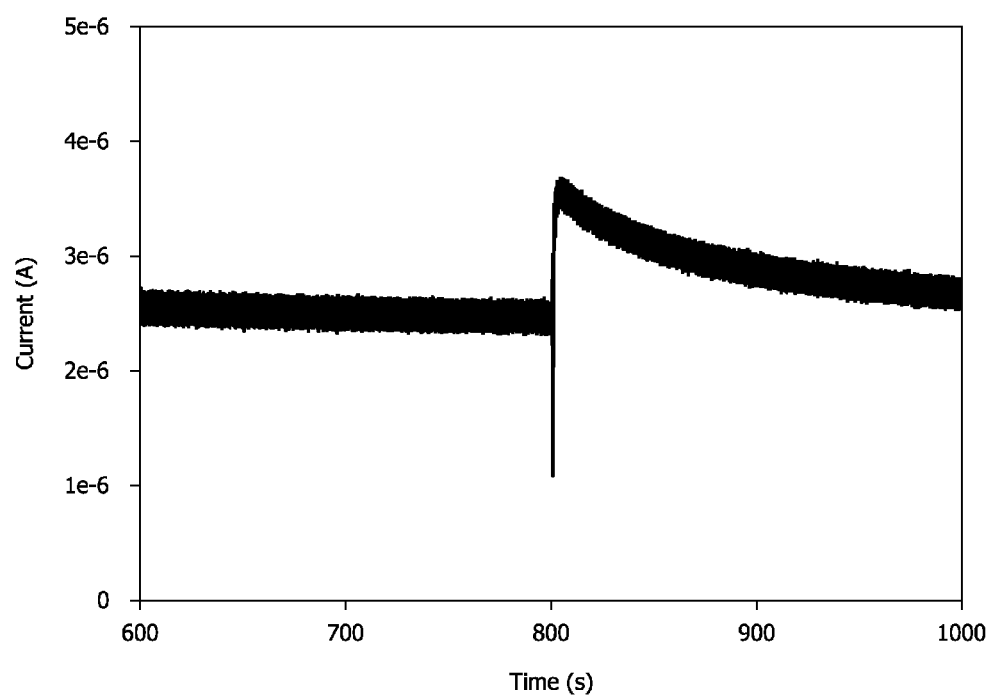
FIG. 10 is a graph showing the current vs. time curve for an ethanol sensor.

A glassy carbon electrode was modified with methylene green which was polymerized by chemical or electrochemical means. Alcohol dehydrogenase was immobilized in a tetrabutylammonium bromide-modified Nafion® membrane using the procedure described above in Example 1 and the immobilized enzyme was layered on the modified glassy carbon electrode and allowed to dry. After the modified glassy carbon electrode dried, it was placed in 1.5 mL of pH 7.15 phosphate buffer and allowed to equilibrate. After equilibration, amperometric sensing was performed at a potential of −0.4V. After a baseline reading was established, 1 mL of 8 mM ethanol solution in phosphate buffer was injected into the solution. FIG. 10 shows the graph of the current vs. time for the amperometric sensor.

DESCRIPTION OF THE RELATED ART

References cited throughout this specification are listed here by number and are incorporated herein by reference. The discussion of references herein is intended merely to summarize the assertions made by their authors and no admission is made that any reference constitutes prior art. Applicants reserve the right to challenge the accuracy and pertinence of the cited references:
1. G. T. R. Palmore; G. M. Whitesides, "Microbial and Enzymatic Biofuel Cells," in ACS Symposium Series 566 (1994) 271-290.
2. M. Schrenk; R. Villigram; N. Torrence; S. Brancato; S. D. Minteer, "Effect of Mixture Casting Nafion® with Quaternary Ammonium Bromide Salts on the Ion-Exchange Capacity and Mass Transport in the Membranes," Journal of Membrane Science 205 (2002) 3-10.
3. T. J. Thomas; K. E. Ponnusamy; N. M. Chang; K. Galmore; S. D. Minteer, "Effects of Annealing on Mixture-Cast Membranes of Nafion® and Quaternary Ammonium Bromide Salts," Journal of Membrane Science, Vol. 213, (2003) 55-66.
4. W. J. Blaedel; R. A. Jenkins, "Study of the Electrochemical Oxidation of Reduced Nicotinamide Adenine Dinucleotide," Analytical Chemistry 47 (1975) 1337-1338.
5. D. Zhou; H. Q. Fang; H. Chen; H. Ju; Y. Wang, "The Electrochemical Polymerization of Methylene Green and its Electrocatalysis for the Oxidation of NADH," Analytica Chimica Acta 329 (1996) 41-48.
6. D. W. Green; H. W. Sun; B. V. Plapp, "Inversion of the Substrate Specificity of Yeast Alcohol Dehydrogenase," Journal of Biological Chemistry 268 (1993) 7792-7798.
7. Worthington, V. "Worthington Enzyme Manual (1988) 16.
8. G. T. R. Palmore; H. Bertschy; S. H. Bergens; G. M. Whitesides, "A Methanol/Dioxygen Biofuel Cell that Uses NAD+-Dependent Dehydrogenases as Catalysts: Application of an Electro-Enzymic Method to Regenerate Nicotinamide Adenine Dinucleotide at Low Overpotentials," Journal of Electroanalytical Chemistry 443 (1998) 155-161.
9. E. V. Plotkin, I. J. Higgins; H. A. O. Hill, "Methanol Dehydrogenase Bioelectrochemical Cell and Alcohol Detector," Biotechnology Letters 3 (1981) 187-192.
10. G. Davis; H. A. O. Hill; W. J. Aston; I. J. Higgins; A. P. F. Turner, "Bioelectrochemical Fuel-Cell and Sensor Based on a Quinoprotein, Alcohol-Dehydrogenase," Enzyme and Microbial Technology 5 (1983) 383-388.
11. P. L. Yue; K. Lowther, "Enzymatic Oxidation of $C_1$-Compounds in a Biochemical Fuel Cell," Chemical Engineering Journal. 33B (1986) 69-77.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. An enzyme immobilized in a non-naturally occurring colloidal immobilization material capable of immobilizing and stabilizing the enzyme, the material being permeable to a compound smaller than the enzyme and the stabilized enzyme retaining at least 75% of its initial catalytic activity while continuously catalyzing a chemical reaction for at least 30 days, wherein the enzyme is entrapped within a pore of the enzyme immobilization material.

2. The immobilized enzyme of claim 1 wherein the immobilization material is an acellular, colloidal immobilization material.

3. An enzyme immobilized in an immobilization material capable of immobilizing and stabilizing the enzyme, the material being permeable to a compound smaller than the enzyme and the stabilized enzyme retaining at least 75% of its initial catalytic activity while continuously catalyzing a chemical reaction for at least 30 days, wherein the enzyme is entrapped within a pore of the enzyme immobilization material and the enzyme immobilization material comprises a micellar or inverted micellar structure.

4. The immobilized enzyme of claim 3 wherein the immobilization material is a cation-modified perfluoro sulfonic acid-PTFE copolymer.

5. The immobilized enzyme of claim 3 wherein the enzyme comprises an alcohol dehydrogenase, aldehyde dehydrogenase, formate dehydrogenase, formaldehyde dehydrogenase, glucose dehydrogenase, glucose oxidase, lactic dehydrogenase, lactose dehydrogenase or pyruvate dehydrogenase.

6. The immobilized enzyme of claim 3 wherein the enzyme is active for at least 90 days.

7. The immobilized enzyme of claim 4 wherein the cation modified perfluoro sulfonic acid-PTFE copolymer is modified with a hydrophobic cation larger than $NH_4^+$.

8. The immobilized enzyme of claim 7 wherein the hydrophobic cation comprises an ammonium-based cation, quaternary ammonium cation, alkyltrimethylammonium cation, organic cation, phosphonium cation, triphenylphosphonium, pyridinium cation, imidazolium cation, hexdecylpyridinium, ethidium, viologen, methyl viologen and benzyl viologen, bis(triphenylphosphine)iminium, metal complex, bipyridyl metal complex, phenanthroline-based metal complex, [Ru (bipyridine)$_3$]$^{2+}$ or [Fe(phenanthroline)$_3$]$^{3+}$.

9. The immobilized enzyme of claim 7 wherein the hydrophobic cation comprises a quaternary ammonium cation represented by formula 1

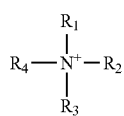
(1)

wherein
R$_1$, R$_2$, R$_3$ and R$_4$ are independently hydrogen, hydrocarbyl, substituted hydrocarbyl or heterocyclo; and
wherein at least one of R$_1$, R$_2$, R$_3$ and R$_4$ is other than hydrogen.

10. The immobilized enzyme of claim 9 wherein R$_1$, R$_2$, R$_3$ and R$_4$ are independently hydrogen, methyl, ethyl, propyl, butyl, pentyl, hexyl, heptyl, octyl, nonyl or decyl wherein at least one of R$_1$, R$_2$, R$_3$ and R$_4$ is other than hydrogen.

11. The immobilized enzyme of claim 9 wherein R$_1$, R$_2$, R$_3$ and R$_4$ are the same and are methyl, ethyl, propyl, butyl, pentyl or hexyl.

12. The immobilized enzyme of claim 9 wherein R$_1$, R$_2$, R$_3$ and R$_4$ are butyl.

13. The immobilized enzyme of claim 3 wherein the compounds smaller than the enzymes comprise ammonia, methanol, ethanol, propanol, isobutanol, butanol and isopropanol, allyl alcohols, aryl alcohols, glycerol, propanediol, mannitol, glucuronate, aldehyde, carbohydrates, glucose, glucose-1, D-glucose, L-glucose, glucose-6-phosphate, lactate, lactate-6-phosphate, D-lactate, L-lactate, fructose, galactose-1, galactose, aldose, sorbose, mannose, glycerate, coenzyme A, acetyl Co-A, malate, isocitrate, formaldehyde, acetaldehyde, acetate, citrate, L-gluconate, beta-hydroxysteroid, alpha-hydroxysteroid, lactaldehyde, testosterone, gluconate, fatty acids, lipids, phosphoglycerate, retinal, estradiol, cyclopentanol, hexadecanol, long-chain alcohols, coniferyl-alcohol, cinnamyl-alcohol, formate, long-chain aldehydes, pyruvate, butanal, acyl-CoA, steroids, amino acids, flavin, NADH, NADH$_2$, NADPH, NADPH$_2$ or hydrogen.

14. A method of catalyzing a reaction in a biofuel cell, a biosensor, a bioprocessor, a bioassay, an enzyme sensor, a bioreactor, enzyme therapy, an immunoassay, or a biomimic comprising catalyzing the reaction with the immobilized enzyme of claim 3.

15. The method of claim 14 wherein the immobilized enzyme catalyzes a reaction in a biofuel cell.

16. The method of claim 14 wherein the immobilized enzyme catalyzes a reaction in a bioprocessor.

17. The method of claim 14 wherein the immobilized enzyme catalyzes a reaction in a bioassay.

18. The method of claim 14 wherein the immobilized enzyme catalyzes a reaction in an enzyme sensor.

19. The method of claim 14 wherein the immobilized enzyme catalyzes a reaction in enzyme therapy.

20. The method of claim 14 wherein the immobilized enzyme catalyzes a reaction in an immunoassay.

* * * * *